United States Patent [19]
Gohbara et al.

[11] Patent Number: 5,498,591
[45] Date of Patent: Mar. 12, 1996

[54] **WEED CONTROL COMPOSITIONS CONTAINING *DRECHSLERA MONOCERAS* AND ADDITIONAL HERBICIDAL AGENTS**

[75] Inventors: Masatoshi Gohbara, Meguro; Kenichi Yamaguchi, Mobara; Tatsuo Shinmi, Mobara; Emi Shinmi, Mobara; Kazunori Takanaka, Mobara; Tomoko Hiruta, Mobara, all of Japan

[73] Assignee: Mitsui Toatsu Chemicals, Incorporated, Tokyo, Japan

[21] Appl. No.: 414,321

[22] Filed: Mar. 31, 1995

Related U.S. Application Data

[62] Division of Ser. No. 214,585, Mar. 18, 1994, Pat. No. 5,434,121.

[30] Foreign Application Priority Data

Mar. 25, 1993 [JP] Japan .................... 5-066398

[51] Int. Cl.$^6$ .................................. A01N 63/04
[52] U.S. Cl. .................. 504/117; 504/118; 504/129; 504/130; 504/133; 504/136; 504/138; 504/143; 504/149; 504/139; 504/140
[58] Field of Search ................... 504/117, 118, 504/129, 130, 133, 136, 138, 139, 140, 143, 149

[56] References Cited

U.S. PATENT DOCUMENTS

| | | | |
|---|---|---|---|
| 3,849,104 | 11/1974 | Daniel et al. | 71/65 |
| 3,999,973 | 12/1976 | Templeton | 71/79 |
| 4,390,360 | 6/1983 | Walker | 71/79 |
| 4,419,120 | 12/1983 | Walker | 71/79 |
| 5,332,573 | 7/1994 | Yamaguchi et al. | 504/117 |
| 5,424,271 | 6/1995 | Yamaguchi et al. | 504/117 |

FOREIGN PATENT DOCUMENTS

| | | |
|---|---|---|
| 4542889 | 6/1990 | Australia . |
| 0207653 | 1/1987 | European Pat. Off. . |
| 0374499 | 6/1990 | European Pat. Off. . |
| 0464416 | 1/1992 | European Pat. Off. . |
| 9006056 | 6/1990 | WIPO . |

OTHER PUBLICATIONS

Jong et al, "American Type Culture Collection Catalogue of Fungi/Yeasts", Seventeenth Edition, 1987, p. 144.

Yu et al, Sol Biol. Biochem. vol. 20, No. 5, pp. 607–612, 1988.

Strobel, et al, Phytoparasitica, vol. 16, No. 2, pp. 145–152, 1988.

Wymore et al, Weed Science, vol. 35, pp. 377–383, 1987.

Klerk et al, Weed Science, vol. 33, No. 1, pp. 95–99, 1985.

D. J. Robeson et al, Agricultural and Biological Chemistry vol. 46, No. 11, 1982 pp. 2681–2683, Agricultual Chemical Society of Japan, Tokyo.

Prete et al. *Biol Abst.* 80(9): 80561. "Seed–Borne Fungi of Weeds" *Summo Phytoethol* 10:260–267. 1984.

Jeffreys. In Jong et al, ATCC of Fungi/Yeasts, 17th ed. #24641. 1987.

*Primary Examiner*—S. Mark Clardy
*Attorney, Agent, or Firm*—Nixon & Vanderhye

[57] ABSTRACT

Described are *Drechslera monoceras* var. *microsporus* strains, that is, new microorganism strains which show herbicidal effects against all varieties of barnyard grass, i.e., *Echinochloa spp.* as weed even at temperatures as low as 15° C. but does not give any influence to cultivation crops such as rice; weed control compositions against barnyard grass, said compositions each containing one of the microorganism strains as an effective ingredient and having high safety and selectivity; and a barnyard grass control method employing at least one of the microorganism strains. Combined use of at least one of the microorganism strains with a chemical herbicide makes it possible to substantially reduce their dosages compared with those required when they are singly applied.

18 Claims, 2 Drawing Sheets

WEED CONTROL COMPOSITIONS CONTAINING *DRECHSLERA MONOCERAS* AND ADDITIONAL HERBICIDAL AGENTS

This is a divisional of application Ser. No. 08/214,585, filed Mar. 18, 1994, now U.S. Pat. No. 5,434,121.

TITLE OF THE INVENTION

New Variety of *Drechslera monoceras*, Weed Control Compositions Containing the Same as an Effective Ingredient and Weed Control Methods Using The Same.

BACKGROUND OF THE INVENTION

1. Field of the Invention

The present invention relates to a new variety of *Drechslera monoceras*, said variety showing no pathogenicity against crops but exhibiting pathogenicity against barnyard grass, weed control compositions containing the same as an effective ingredient and also weed control methods using the same.

2. Description of the Related Art

Serious problems have arisen in last several years from the excessive use of synthesized organic agricultural chemicals, including environmental pollution and reduced effects of control due to the occurrence of diseases, pests and weeds with acquired chemical resistance. Influence of agricultural chemicals to the human body and the natural environment is now increasingly reported to large extents by mass media. Further, the interests in biological control of pests have increased so that a great deal of research and development work is under way with respect to bioinsecticides and bioherbicides. Pesticideless or herbicideless cultivation methods and biological control methods are still in the middle of investigation. As a matter of fact, when applied singly, they cannot provide stable control effects so that no sufficient production of crops can be expected. Whatever control method is used, it is very significant from the viewpoint of safety to lower the dosage of a synthetic organic agricultural chemical.

In the field of herbicides, research and development work has been carried out, centered in the United States, with respect to bioherbicides which use a pathogen against weeds. Bioherbicides which have been put on the market to date include "DeVine" (trade mark; product of Abbott Laboratories Ltd.) and "Collego" (trade mark; product of Ecogen Inc.). The former makes use of *Phytophthora palmivola* which is a pathogen against strangle vine (*Morrenia odorata*), an Asclepiadaceae weed, while the latter utilizes *Colletotrichum Eloeosporioides* which is a pathogen against northern jointvetch (*Aeschynomene virginica*), a leguminous weed. To the best of the present inventors knowledge, no bioherbicide has been put into practical use against barnyard grass (*Echinochloa spp.*) which is a troublesome weed in the cultivation of important crops such as wheat, rice and soybean.

Wild species of barnyard grass are known as weeds in the rice crop areas of the world. Barnyard grass has long been a problem as a typical lowland weed especially in Japan. Occurrence of barnyard grass in paddy fields is said to have led to the need for transplanting of rice seedlings. According to Yabuno ["Zasso Kenkyu (Weed Research), Japan" 20 (1975)], barnyard grass which grows wild in the world includes *Echinochloa oryzicola, Echinochloa colona, Echinochloa pyramidalis, Echinochloa stagnina, Echinochloa haplocloda* and *Echinochloa crus-galli*, and the *crus-galli* species is classified into three varieties, namely, *Echinochloa crus-galli* var. *formosensis, Echinochloa crus-galli* var. *crus-galli, Echinochloa crus-galli* var. *praticola*. Among these varieties, different reactions are observed to herbicides and pathogens. Barnyard grass which grows naturally as a weed is considered to include hybrids of these Echinochloa species. As a herbicide having practical control effects against barnyard grass, it is therefore desired to have herbicidal effects against all the species of *Echinochloa spp.*. Even if herbicidal effects may not be exhibited against all the species of *Echinochloa spp.*, it is required to have a broad herbicidal spectrum against at least practically troublesome species of Echinochloa spp..

When the surrounding temperature exceeds 10° C., weed of *Echinochloa spp.* is allowed to germinate and begins to grow. To achieve more effective control, it is preferred to apply a herbicide at the same time as the time of germination of the weed of *Echinochloa spp.*. In Japanese lowlands, for example, the period of from May to June during which the water temperature arises to 10°–15° C. or so is the time for weed control.

It is therefore preferred for Echinochloa spp. control agents to have a broad herbicidal spectrum against the above-described various species of *Echinochloa spp.* and also to bring about good results even at a temperature as low as about 15° C.

Reported as strains of *Drechslera monoceras sp.* collected from *Echinochloa spp.* include ATCC-24641 [American Type Culture Collection (ATCC) Catalogue of ATCC page 144] as well as IFO-9619 and IFO-9800 [Institute for Fermentation OSAKA (IFO) List of Culture page 177]. As will be described subsequently herein, these strains do not show any herbicidal activities against *Echinochloa spp.* and their esterase zymograms are different from those of the new variety according to the present invention.

Further, as *Drechslera monoceras sp.* capable of showing pathogenicity against *Echinochloa spp.*, European Patent Applications Nos. 0464410A2 and 0374499-A1 disclose eleven (11) strains including MH-9011 (Ferm BP3416) as the most effective strain at 25° C. These strains, as will be described subsequently herein, are also different in esterase zymogram from the new variety according to the present invention and show practically no herbicidal activities at the germination temperature of *Echinochloa spp.*, that is, around 15° C.

To achieve more effective control of *Echinochloa spp.* by a bioherbicide, there is an outstanding demand for the provision of a microorganism which has sufficient *Echinochloa spp.* control effects at temperatures as low as 15° C. or so.

Besides barnyard grass, many weeds grow competitively with crops in lowlands and uplands. Control of these weeds is also essential in practice. To control these many weeds at once, it is the current common practice to use a few types of chemical herbicides in combination. Application of a variety of chemical herbicides in large amounts is however not preferred because as described above, it may result in the occurrence of weeds and insects with acquired herbicide resistance and also in the development of the problem of environmental contamination.

SUMMARY OF THE INVENTION

The present invention has been completed with a view to overcoming the above-described problems of the prior art.

An object of the present invention is therefore to provide a weed control agent and a weed control composition, which can avoid environmental pollution and the occurrence of resistant weeds and moreover, enables practical weed control. In other words, an object of the present invention is to isolate from nature a strain of *Drechslera monoceras sp.*, which exhibits pathogenicity against barnyard grass alone and even at 15° C. and lower, infects all the species of *Echinochloa spp.* to control them, and then to provide a weed control composition containing living fungal cells thereof as an effective ingredient.

Another object of the present invention is to reduce the dosage or application rate of a chemical herbicide by using the chemical herbicide in combination with a new variety of *Drechslera monoceras sp.*, said new variety being capable of exhibiting pathogenicity against barnyard grass alone and also of causing infection even at 15° C. and lower, so that a safer and sufficiently practical weed control composition can be provided.

A further object of the present invention is to provide a weed control method, which makes use of the above new variety of *Drechslera monoceras sp.* and optionally, in combination with a chemical herbicide.

The fungus according to the present invention is taxonomically classified to *Drechslera monoceras sp.* but is a variety clearly different from *Drechslera monoceras sp.* known to date. In the present application, the conventional *monoceras sp.* will be referred to as "*Drechslera monoceras var. monoceras*" while the new variety according to this invention will be referred to as "*Drechslera monoceras var. microsporus*", so that they can be distinguished from each other.

The new variety according to the present invention has been found to have pathogenicity against all the species of *Echinochloa spp.*, said species being barnyard grass as weeds, even at 15° C. and lower and to exhibit practical herbicidal effects against barnyard grass in a period including the time of transplanting rice seedlings in Japan. The new variety has also been confirmed to have extremely high safety for cultivated plants including rice plants. The new variety according to the present invention was collected from natural microorganisms, is completely free from the potential danger of environmental pollution which is a current concern with respect to the use of synthesized organic agricultural chemicals, and is safe.

Further, the mixed composition according to the present invention, which comprises the new variety of *Drechslera monoceras sp.* and a chemical herbicide, can show sufficient control effects in combination at such a small dosage that neither the novel variety nor the chemical herbicide can achieve control when individually applied at the same dosage level. This has made it possible to reduce the dosage of the both herbicides. Moreover, owing to synergistic effects achieved as a result of the mixing of the novel variety of *Drechslera monoceras sp.* with the chemical herbicide, it is possible to reduce the amount of conidia of the variety of *Drechslera monoceras sp.* so that the production cost can be lowered.

As will be appreciated from the foregoing, the novel microorganism, weed control agent and weed control composition, all pertaining to the present invention, contribute not only to the production of crops but also to avoiding environmental pollution and the occurrence of weeds with acquired chemical resistance, which have become problems in recent years.

DETAILED DESCRIPTION OF THE PREFERRED EMBODIMENTS

Figure 1:
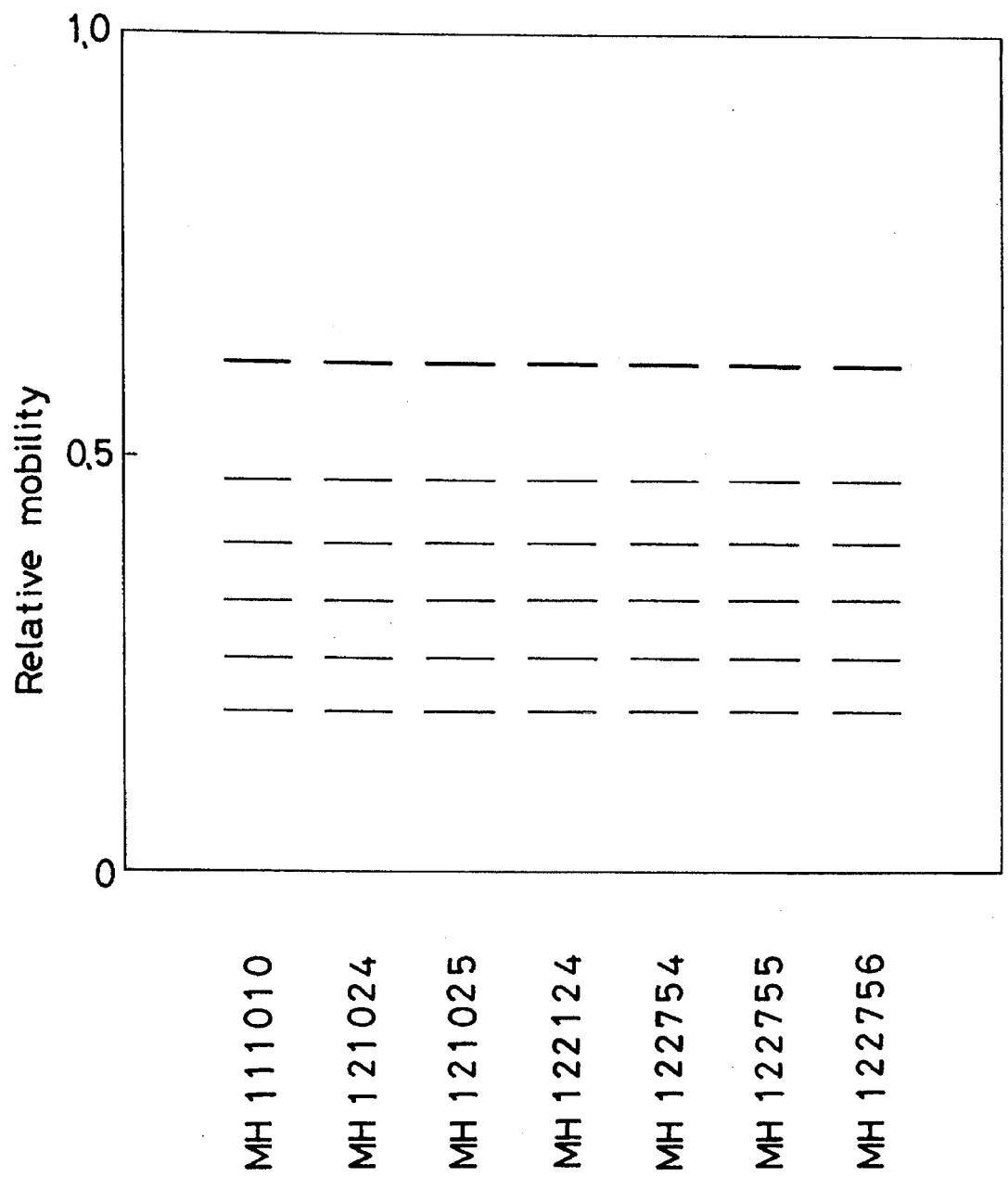
FIG. 1 is a diagram showing zymogrammatic patterns of esterases formed by the new variety according to the present invention.

With a view to controlling barnyard grass, a troublesome weed in lowlands and uplands, the present inventors surveyed a variety of pathogens. As a result, the present inventors has found the new strains of *Drechslera monoceras* sp., which exhibit herbicidal effects against barnyard grass even at 15° C. and lower but do not have pathogenicity against economic crops including rice plants. As a result of various investigations, these strains have been found distinguishable as a new variety clearly different from the conventional strains of *Drechsleramonoceras sp.*, leading to the completion of the present invention. To distinguish the new variety according to the present invention from the conventional strains, they will hereinafter be called "*Drechslera monoceras var. microsporus*" strain and "*Drechslera monoceras var. monoceras* strains, respectively, as described above.

It has also been found that use of the new variety of *Drechslera monoceras sp.*, said new variety having selective pathogenicity against barnyard grass, in combination with a conventional chemical herbicide can bring about significant synergistic effects, and application of the chemical herbicide at a dosage of only one tenth to one hundredth of its conventional published or labelled dosage can still achieve sufficient control effects against barnyard grass.

Barnyard grass, which is the target weed of the present invention, is a weed belonging to the genus Echinochloa, which in turn falls under the order of Graminales. Described specifically, it includes the following varieties: *Echinochloa oryzicola, Echinochloa crus-galii var. formosensis, Echinochloa crus-galli var. crus-galli, Echinochloa crus-galli var. praticola, Echinochloa colona, Echinochlos pyramidalis, Echinochloa stagnina* and *Echinochloa haploclada*.

The new microorganism according to the present invention is a new variety of *Drechslera monoceras*, that is, *Drechslera monoceras var. microsporus* which possesses no pathogenicity against cultivated crops—such as rice, barley, wheat, rye, wild oat, corn, sorghum and foxtail millet—and pastures—such as orchard grass, Italian rye grass, perennial rye grass, sweet barnal grass, tall fescue and meadow fescue—but has pathogenicity against *Echinochloa oryzicola, Echinochloa crus-galli, Echinochloa colonum* and the like.

The new variety was isolated in a pure form from samples of barnyard grass, which were naturally infected. Its pathogenicity was tested against barnyard grass and rice. Based on the results of the test, the new variety having strong pathogenicity against all the varieties of *Echinochloa spp.*, which are barnyard grass weeds, but showed no pathogenecity against rice was selected. The microorganisms so selected were identified on the basis of the morphological characteristics of their conidia according to the conventional classification method established by M. B. Ellis, an analysis of their genes and an analysis of the isozymmatic patterns of their esterases. These analyses distinguish the new variety of *Drechslera monoceras sp.*, that is, *Drechslera monoceras var. microsporus* strain from the conventionally-known strains of *Drechslera monoceras sp.*, that is, *Drechslera monoceras var. monoceras* strains.

The strains of the new variety according to the present invention can be used either singly or in combination as an effective ingredient in a weed control agent. The new variety of this invention can be used as weed control agents in various ways. Living fungal cells obtained by culture of one of the new variety strains can be used directly, i.e., as they are. It is also possible to use a filtrate obtained subsequent to culture of cells. As a further alternative, it is also possible to use both the living fungal cells and the filtrate as a mixture. In addition, each new variety of the present invention can also be used either singly by suspending its conidia and hyphae, which have been obtained by culturing the microorganism on a nutrient medium, in an aqueous solution containing a surfactant or the like or in combination with one or more other agricultural chemicals such as herbicides, fungicides and insecticides, which do not exhibit competition with the microorganism. When the variety according to the present invention is used as weed control agents, conidia having higher durability than hyphae are more desired. Although proliferation of cells of the new variety according to the present invention is feasible whether a liquid medium or a solid medium is used, conidia can be formed by inoculating cells to a liquid medium such as a potato-dextrose medium, allowing the cells to proliferate, disrupting cells so obtained, and then drying the cells so disrupted. In the case of a solid medium, formation of conidia can be promoted by inoculating cells to a potato-dextrose-agar medium or the like, removing grown aerial hyphae and then drying cells so obtained.

The new variety according to the present invention permits mass production of cells such as conidia and/or hyphae as described above, so that it can be used industrially as weed control agents. Further, these weed control agents—when applied, for example, at the time of transplanting of rice seedlings to a paddy field—exhibit herbicidal effects against only barnyard grass as a weed and have pathogenicity against neither cultivated crops such as rice, barley, wheat, rye, wild oat, corn, sorghum and foxtail millet nor pastures such as orchard grass, Italian rye grass, perennial rye grass, sweet barnal grass, tall fescue and meadow fescue. The weed control agents therefore can provide selective herbicidal effects.

Representative strains of the new variety according to the present invention include, for example, *Drechslera sp.* MH-111010, MH-121024, MH-121025, MH-122124, MH-122754, MH-122755 and MH-122756 strains. Under the Budapest Treaty, these strains have already been deposited on the following deposition dates under the following accession numbers with The National Institute of Bioscience and Human-Technology of the Agency of Industrial Science and Technology (renamed Jan. 1, 1993 from the former name, The Fermentation Research Institute), 1–3, Higashi 1-chome, Tsukuba-shi, Ibaraki-ken 305, Japan.

| Strain | Deposition Date | Accession No. |
| --- | --- | --- |
| MH-111010 | May 25, 1992 | FERM BP-3864 |
| MH-121024 | December 16, 1993 | FERM BP-4498 |
| MH-121025 | December 16, 1993 | FERM BP-4499 |
| MH-122124 | December 16, 1993 | FERM BP-4500 |
| MH-122754 | December 16, 1993 | FERM BP-4501 |
| MH-122755 | December 16, 1993 | FERM BP-4502 |
| MH-122756 | December 16, 1993 | FERM BP-4503 |

The most distinguishing characteristic features of the new variety according to the present invention are that it shows the zymogrammatic patterns of esterases shown in FIG. 1, respectively, and that hyphae growth is observed even at temperatures lower than 15° C., for example, at 10° C. or so. Accordingly, strains classified under *Drechslera monoceras* and having these characteristic features are embraced in the present invention.

The new variety according to the present invention is absolutely not effected by a certain chemical herbicide, such as inhibition of hyphae growth and inhibition of spore germination. Their combined use can bring about substantial improvements in the herbicidal effects against barnyard grass.

As a result of further investigations of various herbicides, weed control compositions which comprise in combination at least one of the *Drechslera monoceras* var. *microsporus* strains according to the present invention and at least one chemical herbicide make it possible to control barnyard grass using the combination at a dosage of the chemical herbicide that if used by itself would not provide adequate control. Examples of the conventional chemical herbicide include oxadiazon, dimethametryne, simetryne, chlormethoxynil, dimepiperate, trifluralin, naproanilide, paraquat, pyrazoxyfen, pyrazolate, butachlor, pretilachlor, benthiocarb, mefenacet, molinate, CNP, DBN, MCP, prometryne, benzofenap, propanil, NSK-850, HW-52, clomeprop, esprocarb, bifenox, quinchlorac, buromobutide, bensulfuron methyl, pyrazosulfuron ethyl, and 2,4-D.

Regarding the mechanism of action by each weed control composition according to the present invention, it appears that absorption and transfer of the chemical herbicide may be promoted through invasive scars formed in plant tissues as a result of infection from the Drechslera strain, and infection from the Drechslera strain may also be facilitated in plant tissues damaged by the chemical herbicide. The reduced dosage of the chemical herbicide owing to such synergistic action of the Drechslera strain and the chemical herbicides can improve today's various problems such as environmental pollution and the occurrence of resistant weeds and can substantially benefit not only agricultural producers but also general consumers.

To use as a herbicide each weed control composition according to the present invention, cells of the new variety of *Drechslera spp.* may be used as they are, together with the chemical herbicide in an undiluted form. It is however generally desirable to mix cells of the variety of *Drechslera spp.* and the undiluted chemical herbicide with an inert solid or liquid carrier and then to prepare the resultant mixture into a formulation form commonly employed in the art, such as a granular formulation, a flowable formulation, a wettable powder, an emulsion or a liquid formulation.

Any carriers can be used whether they are solid or liquid, as long as they are usually employed in agricultural and horticultural pesticides and are biologically inert. They should not be limited to any particular ones.

Examples of solid carriers include mineral powders such as clay, talc, bentonite, zeolite, calcium carbonate, diatomaceous earth and white carbon; vegetable flours such as soybean flour and starch; and high molecular compounds such as polyvinyl alcohol and polyalkylene glycol. On the other hand, exemplary liquid carries include various organic solvents such as decane and dodecane; vegetable oils; mineral oils; and water.

The content of the *Drechslera spp.* variety in each weed control composition according to the present invention can, in terms of spores, be $10^2$–$10^{15}$ spores, preferably $10^6$–$10^{12}$ spores per gram.

The content of the chemical herbicide in each weed control composition according to the present invention varies depending on the formulation form. In general, it can be 0.05–50 wt. % in a granular formulation, 1–50 wt. % in a flowable formulation, and 1–90 wt. % in a wettable powder. Its preferred content is 0.5–20 wt. % in a granular formulation, 10–30 wt. % in a flowable formulation, and 10–50 wt. % in a wettable powder. On the other hand, the content of the *Drechslera spp.* variety can, in terms of spores, be $10^2$–$10^{15}$ spores, preferably $10^6$–$10^{12}$ per gram of the effective ingredients in the composition.

Surfactants, binders, stabilizers and the like, which are commonly used as adjuvants in agricultural and horticultural chemicals, can be used either singly or in combination as needed. As stabilizers, an antioxidant and/or a pH regulator may be used by way of example. A light stabilizer may also be used in some instances.

The total content of such adjuvants may range from 0 wt. % to 80 wt. %. The content of the carrier is therefore the value which is obtained by subtracting the contents of the effective ingredients and adjuvants from 100 wt. %.

When the weed control agents and weed control compositions according to the present invention are applied to a field, their dosage can, in terms of the amount of conidia of the *Drechslera spp.* variety, be $10^2$–$10^{15}$ spores per 10 are (1,000 $m^2$), preferably $10^6$–$10^{12}$ spores per 10 are.

The weed control compositions according to the present invention contain one or more of the strains of the new variety, that is, the new variety of *Drechslera spp.* in combination with one or more of the below-described chemical herbicides. These weed control compositions can be used in the form of mixtures with agricultural chemicals such as fungicides, insecticides and plant growth regulators, fertilizers, soil improvers and the like, which have no fungicidal activities against *Drechslera spp.*, to say nothing of their combined application.

Examples of chemical herbicides which can be mixed include: 2,4-dichlorophenoxyacetic acid (2,4-D), 2-methyl-4-chlorophenoxyacetic acid (MCPA), 2,4,5-trichlorophenoxyacetic acid (2,4,5-T), 2-(2,4-dichlorophenoxy)propionic acid (dichlorprop), 2-(2-methyl-4-chlorophenoxy)propionic acid (mecoprop), 2-(2,4,5-trichlorophenoxy)propionic acid (fenoprop), 4-(2,4-dichlorophenoxy)butyric acid (2,4-DB), 4-(2-methyl-4-chlorophenoxy)butyric acid (MCPB), 2-(2-naphthoxy)propionanilide (naproanilide), 2-(1-naphthoxy)N,N-diethylpropionamide (napropamid), methyl (+)-2-[4-(2,4-dichlorophenoxy)phenoxy] propionate (diclofop-methyl), butyl 2-[4-(5-trifluoromethyl-2-pyridyloxy)phenoxy]propionate (fluazifop), methyl 2-[4-(3-chloro-5-trifluoromethyl-2-pyridyloxy)phenoxy] propionate (haloxyfop), 2-propynyl 2-[4-(3,5-dichloro-2-pyridyloxy)phenoxy] propionate (chlorazifop-propynyl), ethyl 2-[4 -(6-chloro-2-quinoxalinyloxy)phenoxy]propionate (quizalofop-ethyl), ethyl 2-[4-(6-chloro-2-benzoxazolyl) phenoxy] propionate (fenoxaprop-ethyl), ethyl 2[ 4-(6-chloro-2-benzothiazolyloxy)phenoxy]propionate (fenthiaprop-ethyl), 2,3,6-trichlorobenzoic acid (2,3,6-TBA), 3,6-dichloro-2-methoxybenzoic acid (dicamba), 2,5-dichloro-3-aminobenzoic acid (amiben), 3,5,6-trichloro-2-methoxybenzoic acid (tricamba), 4 -chloro-2,2-dimethylvaleranilide (monalide), 3,4-dichloropropionanilide (propanil), 3,4-dichloro-2-methylacrylanilide (dicryl), 3,4-dichlorocyclopropane carboxyanilide (cypromid), 3,4-dichloro-2-methylpentananilide (karsil), 3-chloro-2,4-dimethylpentananilide (solan), N-(1,1-dimethylpropynyl)-3,5-dichlorobenzamide (propyzamide), N,N-dimethyl-2,2-diphenylacetamide (diphenamide), N-naphthylphthalamic acid (naptalam), N-(1,1-dimethylbenzyl)-2-bromo-tert.-butylacetamide (buromobutide), 2-benzothiazol-2-yloxy-N-methylacetanilide (mefenasate), N-[3-(1-ethyl-1-methylpropyl)5-isoxazolyl]-2,6-dimethoxybenzamide (benzamizole), 1,1-dimethyl-3-phenylurea (fenuron), 3-(4 -chlorophenyl)-1,1-dimethylurea (monuron), 3-(4-chloro-phenyl)-2,1,1-trimethylisourea (trimeturon), 3-(4-chlorophenyl)-1-methoxy-1-methylurea (monolinuron), 3-(4-chlorophenyl)-1-methyl-1 -(1-methylpropyn-2-yl)urea (buturon), 3-(4-bromophenyl)-1-methoxy-1-methylurea (metobromuron), 1-(2-methylcyclohexyl)-3-phenylurea (siduron), 1,1-dimethyl-3-(3-trifluoromethylphenyl)urea (fluometuron), 3-(3,4-dichlorophenyl)-1,1-dimethylurea (diuron), 3-(3,4-dichlorophenyl)-1-methoxy-1-methylurea (linuron), 3-(3,4-dichlorophenyl)-1-n-butyl-1-methylurea (neburon), 3-(3-chloro-4-methoxyphenyl)-1,1dimethylurea (metoxuron), 3-(4-bromo-3-chlorophenyl)-1-methoxy-1-methylurea (chlorbromuron), 1-(4-difluoro-chloromethylmercapto-3-chlorophenyl)-3,3-dimethylurea (fluothiuron), 3-(3-chloro-4-methylphenyl)-1,1dimethylurea (chlortoluron), 3-[4-(4-chlorophenoxy)phenyl] -1,1-dimethylurea (chloroxuron), 3-[4-(4-methoxyphenoxy)phenyl] -1,1-dimethylurea (difenoxuron), 3-[3-(N-tert.-butylcarbamoyloxy)phenyl]-1,1-dimethylurea (karbutilate), 3-benzoyl-3-(3,4-dichlorophenyl) -1,1-dimethylurea (phenobenzuron), 1-(α, α-dimethyl benzyl)-3-(4-methylphenyl)urea (dymron), 3-(4 -isopropylphenyl)-1,1-dimethylurea (isoproturon) , 3-(2 -benzothiazolyl)-1,3-dimethylurea (methabenzthiazuron), 3-(2-benzothiazolyl)-1-methylurea (benzthiazuron) , 3-(hexahydro -4,7-methanoindan-5-yl)-1,1-dimethylurea (noruron), 3-cyclooctyl-1,1-dimethylurea (cycluron), 1,3-dimethyl-3-(5-trifluoromethyl-1,3,4-thiadiazol-2yl)-urea (thiazfluron), 1-(5-ethylsulfonyl-1,3,4 -thiadiazol-2-yl)-1,3-dimethylurea (sulfodiazol), 3-[5 -(1,1-dimethylethyl)-1,3,4-thiadiazol-2-yl]-1,3-dimethylurea (tebuthiuron), 3-(5-tert.-butylisoxazol-3-yl)-1,1-dimethylurea (isouron), 4-[2-chloro-4-(3,3-dimethylureido)phenyl] -2-tert.-butyl-1,3,4-oxadiazolin -5-one (dimefuron), 3-(5-tert.-butyl-1,3,4-thiadiazol-2 -yl)-4-hydroxy-1-methyl-2-imidazolidone (buthidazole), 2-chloro-4,6-bis(ethylamino)-1,3,5-triazine (simazine), 2-chloro-4-ethylamino-6-isopropylamino-1,3,5-triazine (atrazine), 2-chloro-4,6-bis (isopropylamino)-1,3,5-triazine (propazine), 2-chloro-4-diethylamino-6-ethyl -amino-1,3,5-triazine (trietazine), 2-chloro-4-ethyl -amino-6-tert.-butylamino-1,3,5-triazine (terbuthylazine), 2-(2-chloro-4-ethylamino-1,3,5-triazin-6-yl -amino)-2-methylpropionitrile (cyanazine), 2-chloro-4 -cyclopropylamino-6-isopropylamino-1,3,5-triazine (prefox), 2-[2-chloro-4-(cyclopropylamino)-1,3,5-triazin-6-yl-amino]-2-methylpropionitrile (procyazin), 2-methoxy-4-sec.-butylamino-6-ethylamino-1,3,5-triazine (secbumeton), 2-methoxy-4,6-bis(isopropylamino)-1,3,5-triazine (prometone), 2-methylthio-4,6-bis-(ethylamino) -1,3,5-triazine (simetryne), 2-methylthio-4,6-bis(isopropylamino)-1,3,5-triazine (prometryne), 2-methylthio-4-methylamino-6-isopropylamino-1,3,5-triazine (ametryne), 2-methylthio-4-ethylamino-6-tert.-butylamino-1,3,5-triazine (terbutryne), 2-methylthio-4-isopropylamino-6-(3-methoxypropylamino)-1,3,5-triazine (methoprotryne), 2-methylthio-4-(1,2-dimethylpropyl)-6 -ethylamino-1,3,5-triazine (dimethametryne), 2-methylthio-4-isopropylamino-6-methylamino-1,3,5-triazine (desmetryne), 4-amino-6-tert.-butyl-3-methylthio-1,2,4 -triazin-5(4H)-one (metribuzin), 2-methylthio-4,6-bis(isopropylamino)-1,3,5-triazine (dipropetryn), 2-tert.-butylamino-4-ethylamino-6-methoxyamino-1,3,5-triazine (terbumeton), 2-azido-4-isopropylamino-6-methylthio-1,3,5-triazine (aziprotryne), 4-amino-3 -methyl-6-phenyl-1,2,4- triazin-5(4H)-one (metamintron), 6-tert.-butyl-4-isobutylideneamino-1,2,4-triazin-5(4H)one (isomethiozin), 3-cyclohexyl-6-dimethylamino-1-methyl-1,3,5-triazin-2,4-(1H,3H)-dione (hexazinone), ethyl-N-(4-chloro-6-ethylamino-1,3,5-triazin-2-yl)aminoacetate (eglinazine), ethyl N-(4-chloro-6-isopropylamino-1,3,5-triazin-2-yl)-aminoacetate (proglinazine), 2-chloro-N-isopropylacetanilide (propachlor), N-methoxymethyl-2',6'-diethyl-2-chloroacetanilide (alachlor), 2-chloro-2',6'-diethyl-N-(buthoxymethyl)acetanilide (butachlor), 2-chloro-2'-ethyl-6'-methyl-N -(2-methoxy-1-methylethyl)acetanilide (metolachlor), N,N-diallyl-2-chloroacetamide (allidochlor), 2-chloro-2',6'-dimethyl-N-(2-methoxyethyl)acetanilide (dimethachlor), 2,6-dinitro-N,N-dipropyl-4-trifluoromethylaniline (trifluralin), N-butyl-N-ethyl -2,6-dinitro-4-trifluoromethylaniline (benfluralin), 2,6-dinitro-N-propyl-N-cyclopropyl-4-trifluoromethylaniline (profluralin), N,N-diethyl-2,4 -dinitro-6-trifluoromethyl-m-phenylenediamine (dinitramin), 4-isopropyl-2,6-dinitro-N,N-dipropylaniline (isopropaline), 2,6-dinitro-N-sec.-butyl-4 -tert.-butylaniline (butralin), 4-methylsulfonyl-2,6 -dinitro-N,N-dipropylaniline (nitralin), 3,4-dimethyl-2,6-dinitro-N-1-ethylpropylaniline (pendimethalin), 3,5-dinitro-N,N-dipropylsulfanylamide (oryzalin), N-ethyl-N-(2-methylallyl-2,6-dinitro-4-(trifluoromethyl)aniline (ethalfluralin), N,N-diethyl-2,4-dinitro-6 -trifluoromethyl-m-phenylenediamine (diethamine), 2 -chloro-N-(4-methoxy-6-methyl-1,3,5-triazin-2-ylaminocarbonyl)benzenesulfonamide (chlorsulfuron), methyl 2-[3-(4-methoxy-6-methyl-1,3,5-triazin-2-yl)ureidosulfonyl] benzoate (metsulfurone-methyl), methyl 2-[3-(4,6-dimethylpyrimidin-2-yl)ureidosulfonyl]benzoate (sulfometuron-methyl), methyl 2-[3-(4,6 -dimethoxypyrimidin-2-yl)ureidosulfonyl]benzoate (bensulfuron), 3-(4,6-dimethoxy-1,3,5-triazin-2-yl)-1-[ 2-(2-methoxyethoxy)phenylsulfonyl]urea (cinosulfuron), N-(2-chloroimidazol[1,2-α]pyridin-3-yl sulfonyl)-N' -(4,6-dimethoxy-2-pyrimidyl)urea (TH-913), 1H-pyrazole -5-sulfonamide-N-[(4,6-dimethoxy-2-pyrimidyl)amino -carbonyl)-1-methyl-4-(2-methyl-2H-tetrazole-5-yl]urea (DPX-A8947), 1-[({o-cyclopropylcarbonyl)phenyl})-sulfonyl] -3-(4,6-dimethoxy-2-pyrimidinyl)urea (AC-140), ethyl 2-[3-(4-chloro-6-methoxypyrimidin-2-yl)ureidosulfonyl] benzoate (chlorinuron), 3-[(4-methoxy-6-methyl-1,3,5-triazin-2-yl)ureidosulfonyl] -2-thiophenecarboxylic acid (thiameturon), 3,7-dichloro-8-quinolinecarboxylic acid (quinchlorac), 3,6-dichloro-2-pyridinecarboxylic acid (clopyralid), α-(2-chlorophenyl) -α-(4-chlorophenyl)-5-pyrimidinemethanol (fenarimol), S,S-dimethyl-2-(difluoromethyl)-4-(2 -methylpropyl)-6-trifluoromethyl-3,5-pyridinedicarbothioate (MON-15100 or MON-15126), 4-chloro-5-(methyl -amino)-2-(3-trifluoromethyl)phenyl)-3(2H)-pyridazinone (norflurazon), O,O-bis(1-methylethyl)-S-[2-[(phenylsulfonyl)amino] ethyl]sulfodithioate (bensulide), (+)-2-[ 4,5-dihydro-4-methyl-4-(1-methylethyl)-5-oxo-1H -imidazol-2-yl]-5-methyl-3-pyridinecarboxylic acid (imazamethapyr), 3-[5-(1,1-dimethylethyl)-3-isoxazolyl]-4 -hydroxy-1-methyl-2-imidazolidione (busoxinone), and 2-[ 1-(ethoxyimino)butyl]-3-hydroxy-5-(2H-tetrahydrothio -pyran-3-yl)-2-cyclohexen-1-one (cycloxydim).

In particular, when weed control compositions according to the present invention are used in combination with one or more of herbicides for barnyard grass, for example, one or more of chemical herbicides such as diphenyl ether herbicides, anilide herbicides and thiolcarbamate herbicides, synergistic herbicidal effects which are so large that cannot be expected when they are applied individually can be obtained, thereby making it possible to control barnyard grass at an unexpectedly low dosage.

Further, when weed control compositions according to the present invention are used in combination with one or more of herbicides for broad-leaf weeds, for example, one or more of chemical herbicides such as sulfonylurea herbicides and triazine herbicides, synergistic herbicidal effects which are so large that cannot be expected when they are applied individually can be obtained. It is therefore possible to reduce the dosage of the pathogen, one of the two effective ingredients, and also to lower the dosage of the chemical herbicide. In addition, various lowland weeds can be controlled owing to the broad-spectrum herbicidal effects of the compositions.

Certain weed control compositions according to the present invention, each of which comprises one of the new strains according to the present invention, that is, one of the *Drechslera monoceras* var. *microsporus* strains as the new variety and a chemical herbicide, will hereinafter be described specifically by the following tests and examples. It is however borne in mind that the present invention is by no means limited to them.

Test 1

Isolation and Selection Method of Microorganisms and Their Identification

1) Isolation method of pathogens

To collect and purify the variety according to the present invention, the well-known methods shown in references as below (Mau-Yen Chiang et al., *Plant Disease Vol.* 73, No. 6 page 459 (1989), Orangel L. Borges, Plant Disease Vol. 67, No. 67 page 996 (1983)).

Target leaf spot of barnyard grass was found on leaves in paddy field in Japan. The individual dark brownish leaf spots ranged in length from 1 mm small spots to 20 mm large spots. Over 2500 pieces of leaves of barnyard grass with those leaf spots were collected around the paddy field in several location of Japan. Centering at individual lesions, leaf pieces of 10–20 mm long were cut off. Those leaf pieces of barnyard grass were dipped for 1–2 seconds in a 70% ethyl alcohol solution and then for 10 minutes in a sodium hypochlorite solution having an effective chlorine concentration of 2%, whereby the leaf pieces of barnyard grass were subjected to surface sterilization. The surface-sterilized lesion tissues were washed three times with distilled water and then placed on an agar medium. Static culture was carried out for 72 hours in a thermostatically controlled chamber at 10° C. After culturing, hyphae tips of mold fungi thus grown were subjected to single hyphae isolation under a stereoscopic microscope, followed by purification on a nutrient medium to obtain more than 7,000 strains in total for all of the 1,000 cultures prepared. As representative examples of new microorganisms among those strains, that is, of the new variety according to the present invention, MH-111010, MH-121024, MH-121025, MH-122124, MH-122754, MH-122755 and MH-122756 strains have been reported as the new variety to The Fungal Society of Japan and have also been deposited with National Institute of Bioscience and Human-Technology as stated above. The mold fungi so isolated were tested for pathogenicity against barnyard grass and their safety to rice.

2) Tests for pathogenicity of the isolated microorganisms against barnyard grass and their safety to rice Barnyard grass and rice (varieties: Nipponbare) were allowed to aseptically grow in test tubes to provide test samples. Namely, barnyard grass seeds and rice seeds were dipped for 1–2 seconds in a 70% ethyl alcohol solution and then for 10 minutes in a sodium hypochlorite solution having an effective chlorine concentration of 2%, whereby the seeds were subjected to surface sterilization. The seeds so surface-sterilized were then washed three times with distilled water. The sterilized seeds were then planted in test tubes which contained a pre-sterilized culture medium. They were allowed to grow to the 1.5 leaf stage in a plant growth chamber.

The isolated microorganisms according to the present invention were individually subjected to plate culture at 25° C. for 4 days on a potato-dextrose agar medium. Colonies were punched out along their circumferences by a sterilized cork borer 5 mm in diameter to obtain mycerial discs as seed cell sources.

The mycerial discs were separately placed on the culture medium in the test tubes in which barnyard grass seedlings and rice seedlings were allowed to grow. After incubating them at 15° C. for 10 days in a plant growth chamber, the pathogenicity of each microorganism against barnyard grass and rice was evaluated in accordance with the following 4-stage system ranging from – to +++. The results are summarized in Table 1.

| | |
|---|---|
| +++ | Death |
| ++ | Severe inhibition to the growth |
| + | Some inhibition to the growth |
| – | No effect |

MH-0003, MH-0007, MH-0011, MH-0015 and MH-9011 are *Drechslera sp.*, *Phoma sp.*, *Fusarium sp.*, *Drechslera monoceras* var. *monoceras*, *Drechslera monoceras* var. *monoceras* strains, respectively. They were all tested for comparison, along with the following additional known ATCC-24641 [American Type Culture Collection (ATCC) Catalogue of ATCC, page 144] and IFO-9619 and IFO-9800 [Institute for Fermentation OSAKA (IFO) List of Culture, page 177] as the representatives of the conventional strains.

TABLE 1

Pathogenicity of Isolated Drechslera spp. Strains

| Microorganism | Barnyard grass | Rice |
|---|---|---|
| MH-0003 | – | – |
| MH-0007 | – | ++ |
| MH-0011 | + | ++ |
| MH-0015 | + | – |
| MH-9011 | + | – |
| ATCC-24641 | – | – |
| IFO-9619 | – | – |
| IFO-9800 | – | – |
| MH-111010 | +++ | – |
| MH-121024 | +++ | – |
| MH-121025 | +++ | – |
| MH-122124 | +++ | – |
| MH-122754 | +++ | – |
| MH-122755 | +++ | – |
| MH-122756 | +++ | – |
| Untreated | – | – |

3) Identification of microorganisms

Identification was conducted with respect to the strains which exhibited marked pathogenicity against barnyard grass but had no effects on rice. As a result, each of MH-111010, MH-121024, MH-121025, MH-122124, MH-122754, MH-122755 and MH-122756 strains gave a colony as large as 65–75 mm in diameter and showed irregular growth when subjected to plate culture at 28° C. for 7 days on a malt-agar medium. Those colonies had a grayish black color. Conidia had scars and their sizes were 17–27 (mostly 19–23) μm in width and 35–110 (mostly 70–100) μm in length. Their major axis/minor axis (length/width) ratios were 6.1 or lower (mostly 4.5–5.0) on average. They had a rather straight shape. The great majority of conidia had 4–6 septa. Conidiophores had a straight shape. In the case of the conventionally-known *Drechslera monoceras* var. *monoceras* strains, on the other hand, the sizes of conidia are 16–25 (mostly 17–20) μm in width and 60–150 (mostly 100–120) μm in length and their major axis/minor axis (length/width) ratios were 5.9 or greater (mostly 6.2–6.5) on average. They have a somewhat bent shape. The great majority of conidia have 4–10 (mostly 5–7) septa. Conidiophores have a straight shape. From the above characteristics, MH-111010, MH-121024, MH-121025, MH-122124, MH-122754, MH-122755 and MH-122756 strains are all classified as strains of *Drechslera monoceras*. Compared with the conventional strains, their conidia are different in size, shape, the number of septa and their pathogenicity is also different.

To substantiate differences of the new variety according to the present invention from conventional *Drechsleramonoceras* var. *monoceras* strains, their isozyme patterns of an enzyme were compared in accordance with the Hunter et al. method as will be described hereinafter. Employed as the enzyme was α-esterase which is less affected by the environment.

The new variety according to the present invention and various comparative strains were each separately subjected at 25° C. for 7–10 days under dark conditions to static culture in a potato-sucrose medium, whereby a cell mat was obtained. The cell mat so obtained was washed with distilled water and its weight was measured. The cell mat was then lyophilized in a freezer which was controlled at –80° C. The resulting lyophilizate was added with 1–1.5 volumes of 0.05M tris-hydrochloric acid buffer (pH 7.4) and was then disrupted. The disrupted liquid mixture was filtered and the filtrate was centrifuged at 10,000 rpm, so that a supernatant was obtained as a sample. The amount of proteins in the sample was measured by the Lowry method.

Using a large slab gel electrophoresis bath, a 10% acrylamide gel and a concentrated gel were prepared as a lower layer and an upper layer, respectively. The sample obtained in the manner described above was over-laid to give a protein weight of 50 μg per well. Electrophoresis was then conducted at 30 mA for 2 hours in a running buffer.

The following experimental conditions were used for the electrophoresis:

| Acrylamide gel | 10% gel | Conc. gel |
|---|---|---|
| A | 12 ml | 1.8 ml |
| B | 9 ml | — |
| C | — | 3 ml |
| D | 140 μl | 36 μl |
| TEMD | 20 μl | 12 μl |
| H$_2$O | 15 ml | 7.2 ml |

A: Acrylamide 29.8%
BIS acrylamide 0.2%
B: 1.5 M Tris-HCl (pH 8.8)
C: 0.5 M Tris-HCl (pH 6.8)
D: 10% ammonium persulfate
Sample buffer

| | |
|---|---|
| 0.5 M Tris-HCl (pH 6.8) | 5 ml |
| 0.05% BPB | 2 ml |
| Glycerol | 2 ml |
| H$_2$O | 18 ml |

| Running buffer | |
|---|---|
| 250 mM Tris | |
| 1.92 M Glycine | |

Staining of the esterase in the gel subjected to the electrophoresis was conducted as will be described next. The gel was dipped in a staining solution which had been prepared by adding 2 ml of a 1% α-naphthylacetic acid/50% acetone aqueous solution and 10 mg of Fast Violet B Salt to 100 ml of 0.05M Tris-hydrochloric acid. The staining was conducted for 30 minutes under shaking. After the staining, the gel was washed with distilled water and the mobility of each band was measured.

Figure 2:
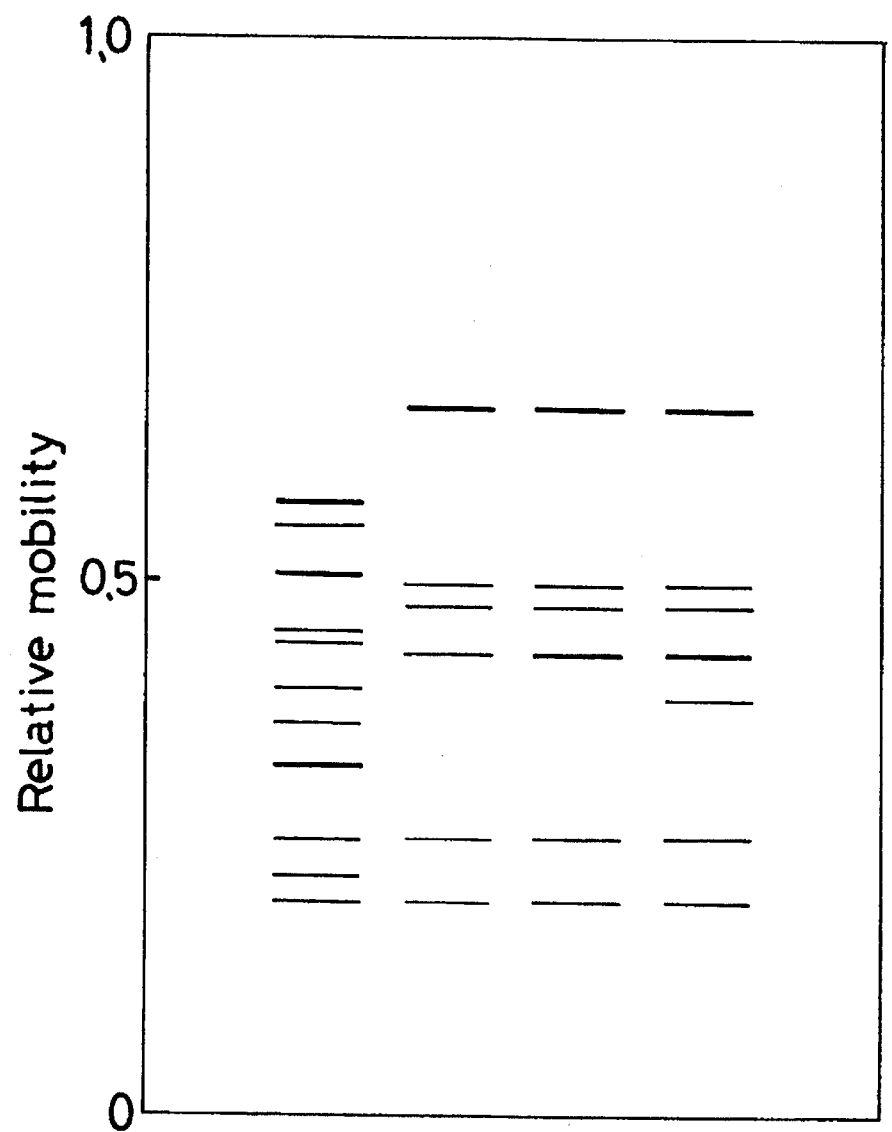
FIG. 2 is a diagram showing zymogrammatic patterns of esterases formed by conventional strains of *Drechslera monoceras sp.*

In FIGS. 1 and 2, zymogrammic patterns of esterases are shown separately corresponding to the individual strains. FIG. 1 shows zymogrammatic patterns of esterases formed by the new variety according to the present invention, whereas FIG. 2 illustrates zymogrammatic patterns of esterases formed by the conventional strains of *Drechsleramonoceras sp*. The results indicate that the new variety according to the present invention is clearly different from the conventional strains of *Drechslera monoceras sp*.

An application of electrophoretic patterns of esterases for the classification of microorganisms, as employed in this test, is routinely conducted in the field of *Basidiomycetes*.

Further, the taxonomic difference between the *Drechslera monoceras* var. *monoceras* strains and the new variety according to the present invention, that is, the *Drechslera monoceras* var. *microsporus* strains has been also confirmed at the level of genes. As a matter of fact, it was possible to observe differences among the varieties even in terms of RNAs coded by their DNAs, respectively.

From the above characteristics, the strains according to the present invention, such as MH-111010, MH-121024, MH-121025, MH-122124, MH-122754, MH-122755 and MH-122756, have been determined as the new variety different from the *Drechslera monoceras* var. *monoceras* strains.

The new variety according to the present invention has been determined not to be pathogens to men under the Pathogens Safety Control Guideline compiled by the National Institutes of Health (Japan).

On the other hand, the strains which did not show any pathogenicity against barnyard grass, that is, MH-003 strain and MH-0007 strain were identified as a *Drechslera sp*. strain and a *Phoma sp*. strain, respectively. The strain which had pathogenicity against both barnyard grass and rice, that is, the MH-0011 strain was identified as a *Fusarium spp*. strain. The strains which had pathogenicity against barnyard grass but did not show any pathogenicity against rice, that is, MH-0015 strain and MH-9011 strain are both known strains of *Drechslera monoceras* var. *monoceras* (EP Publication No. 0464416A2).

The above identification was conducted with reference to M. B. Ellis, "Demariaceus Hyphomycetes", 608, Commonwealth Mycological Institute, Kew, England (1971) and M. B. Ellis "More Demariaceus Hyphomycetes", 507, Commonwealth Mycological Institute, Kew, England (1976).

Test 2

Control Effects of Drechslera Strains against Barnyard Grass

Each *Drechslera* strain isolated from the nature inoculated on an oatmeal-agar medium, followed by static culture at 25° C. for 7 days. Aerial hyphae were then removed with distilled water to promote formation of conidia. The conidia so obtained were suspended in a 0.02% "Triton X-100" (trade name; product of Rohm & Haas Co.) solution to give concentrations of $10^8$ spores/ml and $10^5$ spores/mr, thereby preparing weed control agents containing the Drechslera strain as an effective ingredient.

On the other hand, barnyard grass and rice (varieties: "Nipponbare") were seeded in lowland soil which was contained in 1/10000-are pots, and were reared to the 1.5 leaf stage respectively. After the pots were irrigated to keep the seedlings under submerged conditions of about 5 cm in water depth, the above weed control agents containing conidia of the *Drechslera* strain were separately applied dropwise in an amount of 5 ml per pot. After the seedlings were reared for 10 days in a weather-controlled room which was maintained at 15° C. during the day time and also at night, effects of the Drechslera strain on barnyard grass and rice were evaluated in accordance with the same standard as in Test 1. The results are shown in Table 2.

| | |
|---|---|
| +++ | Death |
| ++ | Severe inhibition to the growth |
| + | Some inhibition to the growth |
| − | No effect |

TABLE 2

Selective Herbicidal Activities of Drechslera spp. - Pot Test

| | Barnyard grass | | Rice | |
|---|---|---|---|---|
| Microorganism | $10^8$ | $10^5$ | $10^8$ | $10^5$ |
| MH-0015 | − | − | − | − |
| MH-9011 | + | − | − | − |
| ATCC-24641 | − | − | − | − |
| IFO-9619 | − | − | − | − |
| IFO-9800 | − | − | − | − |
| MH-111010 | +++ | +++ | − | − |
| MH-121024 | +++ | +++ | − | − |
| MH-121025 | +++ | +++ | − | − |
| MH-122124 | +++ | +++ | − | − |
| MH-122754 | +++ | +++ | − | − |
| MH-122755 | +++ | +++ | − | − |
| MH-122756 | +++ | +++ | − | − |
| Untreated | − | − | − | − |

As a result of the test, MH-111010, MH-121024, MH-121025, MH-122124, MH-122754, MH-122755 and MH-122756 strains of *Drechslera spp*., said strains all pertaining to the present invention, showed herbicidal effects against barnyard grass at the temperature as low as 15° C., which were more than 1,000 times superior to MH-0015 to MH-9011 strains. Further, their safety to rice was also observed.

Test 3

In a similar manner to Tests 1–2), pathogenicity of each microorganism according to the present invention against various species of *Echinochloa spp*. and rice was evaluated. Tested as barnyard grass were *Echinochloa colonum*, *Echinochloa oryzicola*, *Echinochloa crus-galli* var. *formosensis*, *Echinochloa crus-galli* var. *crus-galli* and *Echinochloa crus-galli* var. *praticola*. Tested as rice were "Nipponbare", "Sasanishiki" and "Koshihikari", which are rice species cultivated. Pathogenicity of each microorganism according to the present invention against the barnyard grass and rice was evaluated 10 days after the inoculation. The results are shown in Table 3.

TABLE 3

Pathogenicity of Invention Microorganisms against Various Echinochloa spp.

| | Barnyardgrass | | | | | Rice | | |
|---|---|---|---|---|---|---|---|---|
| Microorganism | Echinochloa oryzicola | Echinochloa crus-galli var. formosensis | Echinochloa crus-galli var. crus-galli | Echinochloa crus-galli var. praticola | Echinochloa colonum | Nippon bare | Sasanishiki | Koshihikari |
| MH-0015 | − | + | + | + | + | − | − | − |
| MH-9011 | − | + | + | + | + | − | − | − |
| ATCC-24641 | − | − | − | − | − | − | − | − |
| IFO-9619 | − | − | − | − | − | − | − | − |
| IFO-9800 | − | − | − | − | − | − | − | − |
| MH111010 | +++ | +++ | +++ | +++ | +++ | − | − | − |
| MH121024 | +++ | +++ | +++ | +++ | +++ | − | − | − |
| MH121025 | +++ | +++ | +++ | +++ | +++ | − | − | − |
| MH122124 | +++ | +++ | +++ | +++ | +++ | − | − | − |
| MH122754 | +++ | +++ | +++ | +++ | +++ | − | − | − |
| MH122755 | +++ | +++ | +++ | +++ | +++ | − | − | − |
| MH122756 | +++ | +++ | +++ | +++ | +++ | − | − | − |
| Untreated | − | − | − | − | − | − | − | − |

+++ Death
++ Severe inhibition to the growth
+ Some inhibition to the growth
− No effect As a result of the test, MH-111010, MH-121024, MH-121025, MH-122124, MH-122754, MH-122755 and MH-122756 as the new variety of *Drechslera monoceras* pertaining to the present invention, had high pathogenicity against all the species and varieties of *Echinochloa spp.* and showed excellent herbicidal effects against them. Further, their safety to rice was also observed.

Test 4

Effects of Chemical Herbicides on Various Biological Properties of *Drechslera spp.*

Mycerial discs of each strain of *Drechslera spp.*, said discs having been prepared by the method described in Test 1–2), were separately placed on layers of a potato-dextrose agar medium, which contained chemical herbicides such as CNP (Herbicide A in tables), mefenacet (Herbicide E in tables), pretilachlor (Herbicide I in tables), benthiocarb (Herbicide L in tables) and bensulfuron (Herbicide P in tables) at the concentration of 500 ppm, respectively. Static culture was then conducted at 25° C. for 5 days. The diameter of each colony so formed was measured and was recorded as a hypha length. Further, spores in aqueous "Triton X-100" solutions of spore suspensions of each strain of *Drechslera spp.*, said solutions having been prepared by the method described in Test 2, were transferred into potato-dextrose liquid media, which contained the individual chemical herbicides at the concentration of 500 ppm, respectively. Static culture was then conducted at 25° C. for 24 hours. After the culture, spore germination was microscopically observed to calculate the rate of spore germination. Effects of each chemical herbicide on the growth of hyphae and the rate of spore germination of each strain of *Drechslera spp.* are expressed in terms of percentage relative to a corresponding control group which did not contain the chemical herbicide. The results are shown in Table 4.

As is apparent from Tables 4-1 and 4-2, neither hyphal growth inhibition nor spore germination inhibition by the chemical herbicides was practically observed with respect to the Drechslera strains according to the present invention.

TABLE 4-1

Effects of Chemical Herbicides against Hyphal Growth of Drechslera spp.

| | Chemical herbicide | | | |
|---|---|---|---|---|
| Microorganism | A | E | I | L |
| MH-0015 | 98 | 96 | 85 | 93 |
| MH-9011 | 98 | 98 | 90 | 100 |
| MH-111010 | 100 | 98 | 95 | 93 |
| MH-121024 | 100 | 100 | 95 | 100 |
| MH-121025 | 100 | 98 | 98 | 96 |
| MH-122124 | 100 | 100 | 100 | 100 |
| MH-122754 | 100 | 97 | 97 | 100 |
| MH-122755 | 100 | 98 | 100 | 96 |
| MH-122756 | 100 | 100 | 95 | 98 |

TABLE 4-2

Effects of Chemical Herbicides against Spore Germination of Drechslera spp.

| | Chemical herbicide | | | | |
|---|---|---|---|---|---|
| Microorganism | A | E | I | L | P |
| MH-0015 | 95 | 97 | 88 | 83 | 100 |
| MH-9011 | 102 | 100 | 98 | 95 | 102 |
| MH-111010 | 100 | 98 | 90 | 90 | 100 |
| MH-121024 | 100 | 100 | 98 | 98 | 100 |
| MH-121025 | 100 | 100 | 95 | 95 | 100 |
| MH-122124 | 100 | 98 | 98 | 98 | 100 |
| MH-122754 | 100 | 100 | 96 | 96 | 100 |
| MH-122755 | 100 | 100 | 98 | 95 | 100 |
| MH-122756 | 100 | 98 | 96 | 98 | 100 |

Test 5

Control Effects of Compositions Containing Drechslera Strain and Chemical Herbicide CNP in Combination Against Barnyard Grass Each *Drechslera monoceras* var. *microporus* strain of the present invention isolated from the nature was inoculated to an oatmeal agar medium, followed by static culture at 25° C. for 7 days. Aerial hyphae were then removed with distilled water to promote formation of conidia. The conidia so obtained were suspended in a 0.02% "Triton X-100" (trade name; product of Rohm & Haas Co.) solution to give prescribed concentrations as shown in Table 5, thereby preparing weed control agents containing the Drechslera strain as an effective ingredient.

Regarding CNP, its 9% granular formulation was weighed in the amounts of 30-1 mg to use it as a chemical herbicide.

On the other hand, barnyard grass and rice (varieties: "Nipponbare") were seeded in lowland soil which was contained in 1/10000-are pots, and were reared to the 1.5 leaf stage respectively. After the pots were irrigated to keep the seedlings under submerged conditions of about 5 cm in water depth, the above weed control agents containing conidia of the Drechslera strain were separately applied dropwise in an amount of 5 ml per pot. At the same time, each pot was treated with the chemical herbicide CNP. After the seedlings were reared for 10 days in a weather-controlled room which was maintained at 15° C. during the day time and at also at night, effects of the Drechslera strain and the chemical herbicide against the barnyard grass and rice were evaluated in accordance with a similar standard to Test 1. The results are shown in Table 5.

| | |
|---|---|
| +++ | Death |
| ++ | Marked inhibition to the growth |
| + | Some inhibition to the growth |
| − | No effect |

Although the results of Table 5 are only one example, the *Drechslera* strain and the chemical herbicide exhibited significant synergistic effects in each combination even at low temperatures.

TABLE 5

| Synergistic Effects of Drechslera spp. and Chemical Herbicides | | | | | |
|---|---|---|---|---|---|
| Microorganism | CNP (mg) | | | | |
| /1/10000 are | 30 | 10 | 3 | 1 | 0 |
| $1 \times 10^6$ spores | 100 (−) | 100 (−) | 100 (−) | 100 (−) | 100 (−) |
| $3 \times 10^5$ spores | 100 (−) | 100 (−) | 100 (−) | 100 (−) | 85 (−) |
| $1 \times 10^5$ spores | 100 (−) | 100 (−) | 100 (−) | 100 (−) | 50 (−) |
| $3 \times 10^4$ spores | 100 (−) | 100 (−) | 100 (−) | 80 (−) | 40 (−) |
| $1 \times 10^4$ spores | 100 (−) | 90 (−) | 70 (−) | 50 (−) | 15 (−) |
| 0 spore | 100 (−) | 60 (−) | 35 (−) | 20 (−) | 0 (−) |

Barnyard grass control value: 0–100%
Sign in parentheses indicates injury against rice and (−) means that no injury was recognized at all.

Formulation examples and herbicidal activity tests of weed control agents according to the present invention will next be described.

Formulation Example 1 (Granular formulation)

After 2 wt. % of "Neopelex" (trade mark; product of Kao Corporation), 2 wt. % of "Sun Ekis P252" (trade name; product of Sanyo-Kokusaku Pulp Co., Ltd.) and 96 wt. % of zeolite were thoroughly mixed, a spore suspension containing $10^9$ conidia of Drechslera MH-111010 strain per gram of a granular formulation to be formulated was added to the resultant mixture to moisten the same. The thus-moistened mass was then extruded into granules by a small extruder. The granules were dried in air, crushed and then processed by a shifting machine, whereby granules of 0.3–2 mm were obtained.

Formulation Example 2 (Granular formulation)

After 2 wt. % of "Neopelex" (trade mark; product of Kao Corporation), 2 wt. % of "Sun Ekis P252" (trade name; product of Sanyo-Kokusaku Pulp Co., Ltd.) and 96 wt. % of zeolite were thoroughly mixed, a spore suspension containing $10^8$ conidia of Drechslera MH-121024 strain per gram of a granular formulation to be formulated was added to the resultant mixture to moisten the same. The thus-moistened mass was then extruded into granules by a small extruder. The granules were dried in air, crushed and then processed by a shifting machine, whereby granules of 0.3–2 mm were obtained.

Formulation Example 3 (Granular formulation)

After 2 wt. % of "Neopelex" (trade mark; product of Kao Corporation), 2 wt. % of "Sun Ekis P252" (trade name; product of Sanyo-Kokusaku Pulp Co., Ltd.) and 96 wt. % of zeolite were thoroughly mixed, a spore suspension containing $10^9$ conidia of Drechslera MH-121025 strain per gram of a granular formulation to be formulated was added to the resultant mixture to moisten the same. The thus-moistened mass was then extruded into granules by a small extruder. The green granules were dried in air, crushed and then processed by a shifting machine, whereby granules of 0.3–2 mm were obtained.

Formulation Example 4 (Granular formulation)

After 2 wt. % of "Neopelex" (trade mark; product of Kao Corporation), 2 wt. % of "Sun Ekis P252" (trade name; product of Sanyo-Kokusaku Pulp Co., Ltd.) and 96 wt. % of zeolite were thoroughly mixed, a spore suspension containing $10^8$ conidia of Drechslera MH-122124 strain per gram of a granular formulation to be formulated was added to the resultant mixture to moisten the same. The thus-moistened mass was then extruded into granules by a small extruder. The granules were dried in air, crushed and then processed by a shifting machine, whereby granules of 0.3–2 mm were obtained.

Formulation Example 5 (Granular formulation)

After 2 wt. % of "Neopelex" (trade mark; product of Kao Corporation), 2 wt. % of "Sun Ekis P252" (trade name; product of Sanyo-Kokusaku Pulp Co., Ltd.) and 96 wt. % of zeolite were thoroughly mixed, a spore suspension containing $10^9$ conidia of Drechslera MH-122754 strain per gram of a granular formulation to be formulated was added to the resultant mixture to moisten the same. The thus-moistened mass was then extruded into granules by a small extruder. The granules were dried in air, crushed and then processed by a shifting machine, whereby granules of 0.3–2 mm were obtained.

Formulation Example 6 (Granular formulation)

After 2 wt. % of "Neopelex" (trade mark; product of Kao Corporation), 2 wt. % of "Sun Ekis P252" (trade name; product of Sanyo-Kokusaku Pulp Co., Ltd.) and 96 wt. % of zeolite were thoroughly mixed, a spore suspension containing $10^8$ conidia of Drechslera MH-122755 strain per gram of a granular formulation to be formulated was added to the resultant mixture to moisten the same. The thus-moistened mass was then extruded into granules by a small extruder. The green granules were dried in air, crushed and then processed by a shifting machine, whereby granules of 0.3–2 mm were obtained.

Formulation Example 7 (Wettable powder)

A mixture of 2 wt. % of "Neopelex" (trade mark; product of Kao Corporation), 2 wt. % of Triton (X-100) and 5 wt. % of white carbon was impregnated with a spore suspension containing $10^{10}$ conidia of Drechslera MH-122756 strain per gram of a wettable powder to be formulated, followed by drying in air. Diatomaceous earth (91 wt. %) was then added, followed by thorough mixing and grinding to obtain the wettable powder.

Formulation Example 8 (Wettable powder)

A mixture of 2 wt. % of "Neopelex" (trade mark; product of Kao Corporation; sodium dodecylbenzenesulfonate), 1 wt. % of "Neugen EA 80" (trade name, product of Sanyo Chemical Industries, Ltd.; polyoxyethylenenonylphenyl ether), 5 wt. % of white carbon and 92 wt. % of diatomaceous earth was impregnated with a spore suspension containing $10^9$ conidia of Drechslera MH-111010 strain per gram of a wettable powder to be formulated, followed by drying in air. The resultant mixture was thoroughly mixed and ground to obtain the wettable powder.

Formulation Example 9 (Wettable powder)

A mixture of 2 wt. % of "Neopelex" (trade mark; product of Kao Corporation), 2 wt. % of Triton (X-100) and 5 wt. % of white carbon was impregnated with a spore suspension containing $10^{10}$ conidia of Drechslera MH-122756 strain per gram of a wettable powder to be formulated, followed by drying in air. Diatomaceous earth (91 wt. %) was then added, followed by thorough mixing and grinding to obtain the wettable powder.

Formulation Example 10 (Wettable powder)

A mixture of 2 wt. % of "Neopelex" (trade mark; product of Kao Corporation; sodium dodecylbenzenesulfonate), 1 wt. % of "Neugen EA 80" (trade name, product of Sanyo Chemical Industries, Ltd.; polyoxyethylenenonylphenyl ether), 5 wt. % of white carbon and 92 wt. % of diatomaceous earth was impregnated with a spore suspension containing $10^9$ conidia of Drechslera MH-121024 strain per gram of a wettable powder to be formulated, followed by drying in air. The resultant mixture was thoroughly mixed and ground to obtain the wettable powder.

Formulation Example 11 (Wettable powder)

A mixture of 2 wt. % of "Neopelex" (trade mark; product of Kao Corporation; sodium dodecylbenzenesulfonate), 1 wt. % of "Neugen EA 80" (trade name, product of Sanyo Chemical Industries, Ltd.; polyoxyethylenenonylphenyl ether), 5 wt. % of white carbon and 92 wt. % of diatomaceous earth was impregnated with a spore suspension containing $10^9$ conidia of Drechslera MH-121025 strain per gram of a wettable powder to be formulated, followed by drying in air. The resultant mixture was thoroughly mixed and ground to obtain the wettable powder.

Formulation Example 12 (Flowable formulation)

"Sun Ekis P252" (10 wt. %) dissolved in 80 wt. % of water was wet-ground, followed by the addition of 0.4 wt. % of "Kelzan S" (trade name; product of Kelco Corp.) dissolved in 9.6 wt. % of a spore suspension which contained $10^{10}$ conidia of Drechslera MH-122754 strain per milliliter of a flowable formulation to be obtained. The resultant mixture was mixed to obtain the flowable formulation.

Formulation Example 13 (Flowable formulation)

After 10 wt. % of "Sun Ekis P252" (trade name; described above) dissolved in 70 wt. % of water was mixed with 10 wt. % of a spore suspension which contained $10^{10}$ conidia of Drechslera MH-111010 per milliliter of a flowable formulation to be obtained, the resultant mixture was wet-ground. Then, 0.2 wt. % of "Kelzan S" (trade name; product of Kelco Corp.; xanthan gum) dissolved in 9.8 wt. % of water was added to obtain the flowable formulation.

Formulation Example 14 (Flowable formulation)

"Sun Ekis P252" (10 wt. %) dissolved in 80 wt. % of water was wet-ground, followed by the addition of 0.4 wt. % of "Kelzan S" (trade name; product of Kelco Corp.) dissolved in 9.6 wt. % of a spore suspension which contained $10^{10}$ conidia of Drechslera MH-122756 strain per milliliter of a flowable formulation to be obtained. The resultant mixture was mixed to obtain the flowable formulation.

Formulation Example 15 (Flowable formulation)

After 10 wt. % of "Sun Ekis P252" (trade name; described above) dissolved in 70 wt. % of water was mixed with 10 wt. % of a spore suspension which contained $10^{10}$ conidia of Drechslera MH-121024 per milliliter of a flowable formulation to be obtained, the resultant mixture was wet-ground. Then, 0.2 wt. % of "Kelzan S" (trade name; product of Kelco Corp.; xanthan gum) dissolved in 9.8 wt. % of water was added to obtain the flowable formulation.

Formulation Example 16 (Flowable formulation)

"Sun Ekis P252" (10 wt. %) dissolved in 80 wt. % of water was wet-ground, followed by the addition of 0.4 wt. % of "Kelzan S" (trade name; product of Kelco Corp.) dissolved in 9.6 wt. % of a spore suspension which contained $10^{10}$ conidia of *Drechslera* MH-122124 strain per milliliter of a flowable formulation to be obtained. The resultant mixture was mixed to obtain the flowable formulation.

Formulation Example 17 (Flowable formulation)

After 10 wt. % of "Sun Ekis P252" (trade name; described above) dissolved in 70 wt. % of water was mixed with 10 wt. % of a spore suspension which contained $10^{10}$ conidia of *Drechslera* MH-121025 per milliliter of a flowable formulation to be obtained, the resultant mixture was wet-ground. Then, 0.2 wt. % of "Kelzan S" (trade name; product of Kelco Corp.; xanthan gum) dissolved in 9.8 wt. % of water was added to obtain the flowable formulation.

Formulation Example 18 (Dry flowable formulation)

Sodium alkylbenzenesulfonate (15 wt. %), polypropylene glycol polyethylene glycol ether (85 wt. %) and $10^{10}$ conidia of *Drechslera* MH-111010 strain per gram of a dry flowable formulation to be obtained were mixed to obtain the dry flowable formulation.

Formulation Example 19 (Dry flowable formulation)

Sodium alkylbenzenesulfonate (15 wt. %), polypropylene glycol polyethylene glycol ether (85 wt. %) and $10^{10}$ conidia of Drechslera MH-121024 strain per gram of a dry flowable formulation to be obtained were mixed to obtain the dry flowable formulation.

Formulation Example 20 (Dry flowable formulation)

Sodium alkylbenzenesulfonate (15 wt. %), polypropylene glycol polyethylene glycol ether (85 wt. %) and $10^{10}$ conidia of Drechslera MH-122754 strain per gram of a dry flowable formulation to be obtained were mixed to obtain the dry flowable formulation.

Formulation Example 21 (Dry flowable formulation)

Sodium alkylbenzenesulfonate (15 wt. %), polypropylene glycol polyethylene glycol ether (85 wt. %) and $10^{10}$ conidia of *Drechslera* MH-122756 strain per gram of a dry flowable formulation to be obtained were mixed to obtain the dry flowable formulation.

Formulation Example 22 (Dust)

"Emulgen 910" (trade name; product of Kao Corporation; polyoxyethylenenonyl phenyl ether; 0.5 wt. %) and kaolin clay (99.5 wt. %) were thoroughly ground and mixed, followed by the addition of $10^8$ conidia of Drechslera MH-111010 per gram of a dust to be obtained. The dust was hence obtained.

Formulation Example 23 (Emulsion)

In a mixture of 5 wt. % of lecithin and 94 wt. % of heavy white oil, $10^{10}$ conidia of *Drechslera* MH-121024 strain were suspended per gram of an emulsion to be formulated. An equiamount of 1 wt. % Triton X-100 was added to the suspension. The resultant mixture was mixed and emulsified to obtain the emulsion.

Formulation Example 24 (Granular formulation)

After 9 wt. % of the finely ground chemical herbicide, CNP (Herbicide A in tables), 2 wt. % of "Neopelex" (trade mark; product of Kao Corporation), 2 wt. % of "Sun Ekis P252" (trade name; product of Sanyo-Kokusaku Pulp Co., Ltd.) and 87 wt. % of zeolite were thoroughly mixed, a spore suspension containing $10^8$ conidia of Drechslera MH-122754 strain per gram of a granular formulation to be formulated was added to the resultant mixture to moisten the same. The thus-moistened mass was then extruded into green granules by a small extruder. The green granules were dried in air, crushed and then processed by a shifting machine, whereby granules of 0.3–2 mm were obtained.

Formulation Example 25 (Granular formulation)

After 3.5 wt. % of the chemical herbicide, butachlor (Herbicide H in tables), 2 wt. % of "Neopelex" (trade mark; product of Kao Corporation), 2 wt. % of "Sun Ekis P252" (trade name; product of Sanyo-Kokusaku Pulp Co., Ltd.) and 92.5 wt. % of zeolite were thoroughly mixed, a spore suspension containing $10^8$ conidia of MH-121025 per gram of a granular formulation to be formulated was added to the resultant mixture to moisten the same. The thus-moistened mass was then extruded into green granules by a small extruder. The green granules were dried in air, crushed and then processed by a shifting machine, whereby granules of 0.3–2 mm were obtained.

Formulation Example 26 (Granular formulation)

After 4 wt. % of the finely ground chemical herbicide, mefenasate (Herbicide E in tables), 2 wt. % of "Neopelex" (trade mark; product of Kao Corporation), 2 wt. % of "Sun Ekis P252" (trade name; product of Sanyo-Kokusaku Pulp Co., Ltd.) and 92 wt. % of zeolite were thoroughly mixed, a spore suspension containing $10^8$ conidia of Drechslera MH-121024 strain per gram of a granular formulation to be formulated was added to the resultant mixture to moisten the same. The thus-moistened mass was then extruded into green granules by a small extruder. The green granules were dried in air, crushed and then processed by a shifting machine, whereby granules of 0.3–2 mm were obtained.

Formulation Example 27 (Granular formulation)

After 0.2 wt. % of the finely ground chemical herbicide, bensulfuron (Herbicide P in tables), 2 wt. % of "Neopelex" (trade mark; product of Kao Corporation), 2 wt. % of "Sun Ekis P252" (trade name; product of Sanyo-Kokusaku Pulp Co., Ltd.) and 95.8 wt. % of zeolite were thoroughly mixed, a spore suspension containing $10^8$ conidia of Drechslera MH-111010 strain per gram of a granular formulation to be formulated was added to the resultant mixture to moisten the same. The thus-moistened mass was then extruded into green granules by a small extruder. The green granules were dried in air, crushed and then processed by a shifting machine, whereby granules of 0.3–2 mm were obtained.

Formulation Example 28 (Granular formulation)

After 0.3 wt. % of the finely ground chemical herbicide, pyrazosulfron ethyl (Herbicide Q in tables), 2 wt. % of "Gosenol GL-05s" (product of The Nippon Synthetic Chemical Industry Co., Ltd.; PVA), 2 wt. % of "Sun Ekis P252" (trade name; product of Sanyo-Kokusaku Pulp Co., Ltd.; sodium lignin sulfonate) and 95.7 wt. % of clay were thoroughly mixed, a spore suspension containing $10^8$ conidia of Drechslera MH-111010 per gram of a granular formulation to be formulated was added to the resultant mixture to moisten the same. The thus-moistened mass was then extruded into green granules by a small extruder. The green granules were dried in air, crushed and then processed by a shifting machine, whereby granules of 0.3–1 mm were obtained.

Formulation Example 29 (Granular formulation)

After 1.5 wt. % of the finely ground chemical herbicide, oxadiazon (Herbicide D in tables), 2 wt. % of "Gosenol GL-05s" (product of The Nippon Synthetic Chemical Industry Co., Ltd.; PVA), 2 wt. % of "Sun Ekis P252" (product of Sanyo-Kokusaku Pulp Co., Ltd.; sodium lignin sulfonate)

and 94.5 wt. % of clay were thoroughly mixed, a spore suspension containing $10^8$ conidia of Drechslera MH-122755 per gram of a granular formulation to be formulated was added to the resultant mixture to moisten the same. The thus-moistened mass was then extruded into green granules by a small extruder. The green granules were dried in air, crushed and then processed by a shifting machine, whereby granules of 0.3–1 mm were obtained.

Formulation Example 30 (Granular formulation)

After 1.5 wt. % of the finely ground chemical herbicide, simetryne (Herbicide S in tables), 2 wt. % of "Gosenol GL-05s" (product of The Nippon Synthetic Chemical Industry Co., Ltd.; PVA), 2 wt. % of "Sun Ekis P252" (product of Sanyo-Kokusaku Pulp Co., Ltd.; sodium lignin sulfonate) and 94.5 wt. % of clay were thoroughly mixed, a spore suspension containing $10^8$ conidia of Drechslera MH-122756 per gram of a granular formulation to be formulated was added to the resultant mixture to moisten the same. The thus-moistened mass was then extruded into green granules by a small extruder. The green granules were dried in air, crushed and then processed by a shifting machine, whereby granules of 0.3–1 mm were obtained.

Formulation Example 31 (Granular formulation)

After 6 wt. % of the chemical herbicide, molinate (Herbicide N in tables), 2 wt. % of "Neopelex" (trade mark; product of Kao Corporation), 2 wt. % of "Sun Ekis P252" (product of Sanyo-Kokusaku Pulp Co., Ltd.; sodium lignin sulfonate) and 90 wt. % of zeolite were thoroughly mixed, a spore suspension containing $10^8$ conidia of *Drechslera* MH-111010 per gram of a granular formulation to be formulated was added to the resultant mixture to moisten the same. The thus-moistened mass was then extruded into green granules by a small extruder. The green granules were dried in air, crushed and then processed by a shifting machine, whereby granules of 0.3–2 mm were obtained.

Formulation Example 32 (Wettable powder)

A mixture of 30 wt. % of the chemical herbicide, chlormethoxynil (Herbicide B in tables), 2 wt. % of "Neopelex" (trade mark; product of Kao Corporation), 2 wt. % of Triton (X-100) and 5 wt. % of white carbon was impregnated with a spore suspension containing $10^9$ conidia of Drechslera MH-122124 per gram of a wettable powder to be formulated. Air-dried diatomaceous earth (61 wt. %) was then added to the mixture so impregnated. They were then thoroughly ground to obtain the wettable powder.

Formulation Example 33 (Wettable powder)

A mixture of 40 wt. % of the chemical herbicide, propanil (Herbicide J in tables), 2 wt. % of "Neopelex" (trade mark; product of Kao Corporation), 2 wt. % of Triton (X-100) and 5 wt. % of white carbon was impregnated with a spore suspension containing $10^9$ conidia of Drechslera MH-121024 per gram of a wettable powder to be formulated. Air-dried diatomaceous earth (51 wt. %) was then added to the mixture so impregnated. They were then thoroughly ground to obtain the wettable powder.

Formulation Example 34 (Wettable powder)

A mixture of 20 wt. % of the chemical herbicide, benthiocarb (Herbicide L in tables), 2 wt. % of "Neopelex" (trade mark; product of Kao Corporation), 2 wt. % of Triton (X-100) and 5 wt. % of white carbon was impregnated with a spore suspension containing $10^9$ conidia of Drechslera MH-111010 strain per gram of a wettable powder to be formulated. Air-dried diatomaceous earth (71 wt. %) was then added to the mixture so impregnated. They were then thoroughly ground to obtain the wettable powder.

Formulation Example 35 (Wettable powder)

A mixture of 40 wt. % of the chemical herbicide, naproanilide (Herbicide F in tables), 2 wt. % of "Neopelex" (trade mark; product of Kao Corporation; sodium dodecylbenzenesulfonate), 1 wt. % of "Neugen EA 80" (trade name, product of Sanyo Chemical Industries, Ltd.; polyoxyethylenenonylphenyl ether), 5 wt. % of white carbon and 52 wt. % of diatomaceous earth was impregnated with a spore suspension containing $10^9$ conidia of Drechslera MH-122124 strain per gram of a wettable powder to be formulated, followed by thorough mixing and grinding to obtain the wettable powder.

Formulation Example 36 (Wettable powder)

A mixture of 20 wt. % of the chemical herbicide, dimepiperate (Herbicide M in tables), 2 wt. % of sodium alkylbenzenesulfonate, 1 wt. % of polyoxyethylene alkylphenylether and 77 wt. % of zeaklite was impregnated with a spore suspension containing $10^9$ conidia of *Drechslera* MH-122754 strain per gram of a wettable powder to be formulated, followed by thorough mixing and grinding to obtain the wettable powder.

Formulation Example 37 (Wettable powder)

A mixture of 40 wt. % of the chemical herbicide, clomeprop (Herbicide K in tables), 5 wt. % of white carbon, 6 wt. % of polyoxyethylene alkylphenylether ammonium sulfate salt, 2 wt. % of sodium lignin sulfonate and 47 wt. % of diatomaceous earth was thoroughly mixed and ground by a Jet-O-Miser, followed by impregnation with a spore suspension containing $10^9$ conidia of Drechslera MH-121024 per gram of a wettable powder to be formulated. The resultant mixture was thoroughly mixed and ground to obtain the wettable powder.

Formulation Example 38 (Flowable formulation)

After 45 wt. % of the finely ground chemical herbicide, CNP (Herbicide A in tables) and 10 wt. % of "Sun Ekis P252" dissolved in 35 wt. % of water were mixed and wet-ground, 0.4 wt. % of "Kelzan S" (trade name: product of Kelco Corp.) dissolved in 9.6 wt. % of a spore suspension containing $10^9$ conidia of Drechslera MH-111010 strain per milliliter of a flowable formulation to be formulated was added to the resultant mixture. The thus-obtained mixture was then mixed to obtain the flowable formulation.

Formulation Example 39 (Flowable formulation)

After 10 wt. % of the chemical herbicide, pretilachlor (Herbicide I in tables) and 10 wt. % of "Sun Ekis P252" dissolved in 70 wt. % of water were mixed and wet-ground, 0.4 wt. % of "Kelzan S" (trade name: product of Kelco Corp.) dissolved in 9.6 wt. % of a spore suspension containing $10^9$ conidia of Drechslera MH-122754 strain per milliliter of a flowable formulation to be formulated was added to the resultant mixture. The thus-obtained mixture was then mixed to obtain the flowable formulation.

Formulation Example 40 (Flowable formulation)

After 56.7 wt. % of water was added to the mixture of 30 wt. % of the chemical herbicide, benthiocarb (Herbicide L in tables), 2 wt. % of sodium lignin sulfonate; 0.3 wt. % of xanthan gum and 1 wt. % of polyoxyethylene alkylarylether, 10 wt. % of a spore suspension containing $10^9$ conidia of Drechslera MH-121024 strain per milliliter of a flowable formulation to be formulated was added to the resultant mixture. The thus-obtained mixture was then finely ground by a sand grinder to obtain the flowable formulation.

Formulation Example 41 (Flowable formulation)

After 30 wt. % of the chemical herbicide, esprocarb (Herbicide O in tables), 10 wt. % of "Sun Ekis P252" (trade name; described above) dissolved in 40 wt. % of water and 10 wt. % of a spore suspension containing $10^9$ conidia of Drechslera MH-122756 strain per milliliter of a flowable formulation to be formulated were mixed, the resultant mixture was mixed and wet-ground. Then 0.4 wt. % of "Kelzan S" (trade name: product of Kelco Corp.; xanthan gum) dissolved in 9.6 wt. % of water was added to the mixture to obtain the flowable formulation.

Formulation Example 42 (Dry flowable formulation)

The finely-ground chemical herbicide, pyrazolate (Herbicide R in tables; 60 wt. %), sodium alkylbenzenesulfonate (5 wt. %), polypropylene glycol polyethylene glycol ether (35 wt. %) and $10^9$ conidia of Drechslera MH-111010 per gram of the chemical herbicide were mixed to obtain the dry flowable formulation.

Formulation Example 43 (Dust)

The finely-ground chemical herbicide, bensulfuron (Herbicide P in tables; 0.2 wt. %), "Emulgen 910" (trade name; product of Kao Corporation; polyoxyethylenenonyl phenyl ether; 0.5 wt. %) and kaolin clay (99.3 wt. %) were thoroughly mixed and ground, followed by the addition of $10^8$ conidia of Drechslera MH-111010 strain per gram of a dust to be obtained. The dust was hence obtained.

Formulation Example 44 (Dust)

The finely-ground chemical herbicide, mefenacet (Herbicide E in tables; 4 wt. %), "Emulgen 910" (trade name; product of Kao Corporation; polyoxyethylenenonyl phenyl ether; 1 wt. %), sodium lignin sulfonate (3 wt. %), polyoxyethylene alkylarylether (2 wt. %) and clay (90 wt. %) were mixed and ground, followed by the addition of $10^9$ conidia of *Drechslera* MH-121024 per gram of a dust to be obtained. The dust was hence obtained.

Formulation Example 45 (Emulsion)

In a mixture of 1 wt. % of the chemical herbicide, bensulfuron (Herbicide P in tables), 5 wt. % of lecithin and 94 wt. % of heavy white oil, $10^9$ conidia of Drechslera MH-111010 strain were suspended per milliliter of an emulsion to be formulated. An equiamount of 1 wt. % Triton X-100 was added to the suspension. The resultant mixture was mixed and emulsified to obtain the emulsion.

Formulation Example 46 (Emulsion)

In a mixture of 2 wt. % of the chemical herbicide, biphenox (Herbicide C in tables), 5 wt. % of lecithin and 92 wt. % of heavy white oil, $10^{10}$ conidia of Drechslera MH-122756 were suspended per milliliter of an emulsion to be formulated. An equiamount of 1 wt. % Triton X-100 was added to the suspension. The resultant mixture was mixed and emulsified to obtain the emulsion.

In addition to the above formulation examples, formulation was conducted with respect to the combinations of conidia of various strains and various chemical herbicides. It is therefore to be noted that formulations are not limited to those exemplified above.

Example 1

Herbicidal Effects by Weed Control Compositions of New Microorganism Strains According to the Invention and Chemical Herbicides, against Barnyard Grass—Granular Formulations Barnyard grass seeds were planted in lowland soil which was contained in 1/1000-are pots, and the plants raising from the seeds were reared to the 1.5 leaf stage. The plants were irrigated to keep about 5 cm depth in water and treated with 30 mg (equivalent to one tenth of the standard dosage) of the granular formulations prepared as described in Formulation Examples 24–31 except that the various strains and chemical herbicides were used. The plants were then allowed to grow in a green house which was maintained at 15° C. during the day time and also at night. Twenty days after the treatment, the remaining populations in the individual pots were counted. The control values against barnyard grass were calculated in accordance with the following formula and are shown in Tables 6-1 to 6-3.

$$\text{Control value} = \frac{\text{Remaining population in untreated group} - \text{Remaining population in treated group}}{\text{Remaining population in untreated group}} \times 100$$

In the tables, letters A–O represent the following herbicides. Their dosages are also shown in the parentheses.

|  | Dosages (g/10 are) |
|---|---|
| A: CNP | (27) |
| B: Chlormethoxynil | (21) |
| C: Bifenox | (21) |
| D: Oxadiazon | (6) |
| E: Mefenasate | (12) |
| F: Naproanilide | (30) |
| G: NSK-850 | (2) |
| H: Butachlor | (15) |
| I: Pretilachlor | (6) |
| J: Propanil | (50) |
| K: Clomeprop | (4.5) |
| L: Benthiocarb | (21) |
| M: Dimepiperate | (21) |
| N: Molinate | (24) |
| O: Esprocarb | (21) |

The same test as above was conducted using each of MH-0015 & MH-9011 at the same conidia number.

TABLE 6-1

Herbicidal Effects by Compositions of New Microorganism Strains According to the Invention and Chemical Herbicides of the Diphenyl Ether Type

| Microorganism | Chemical herbicide |||||
|---|---|---|---|---|---|
| | —**) | A | B | C | D |
| —*) | 0 | 10 | 15 | 10 | 20 |
| MH-0015 | 0 | 10 | 25 | 20 | 30 |
| MH-9011 | 0 | 10 | 25 | 20 | 30 |
| MH-111010 | 10 | 100 | 100 | 100 | 100 |
| MH-121024 | 10 | 100 | 100 | 100 | 100 |
| MH-121025 | 10 | 100 | 100 | 100 | 100 |
| MH-122124 | 10 | 100 | 100 | 100 | 100 |
| MH-122754 | 10 | 100 | 100 | 100 | 100 |
| MH-122755 | 10 | 100 | 100 | 100 | 100 |
| MH-122756 | 10 | 100 | 100 | 100 | 100 |

*)in the case where a microorganism was not contained.
**)in the case where a chemical herbicide was not contained.

TABLE 6-2

Herbicidal Effects by Compositions of New Microorganism Strains According to the Invention and Chemical Herbicides of the Anilide Type

| Micro-organism | Chemical herbicide ||||||||
|---|---|---|---|---|---|---|---|---|
| | —**) | E | F | G | H | I | J | K |
| —*) | 0 | 25 | 5 | 30 | 10 | 20 | 5 | 10 |
| MH-0015 | 5 | 25 | 10 | 30 | 10 | 25 | 10 | 10 |
| MH-9011 | 5 | 30 | 25 | 35 | 20 | 25 | 10 | 20 |
| MH-111010 | 10 | 100 | 100 | 100 | 100 | 100 | 100 | 100 |
| MH-121024 | 10 | 100 | 100 | 100 | 100 | 100 | 100 | 100 |
| MH-121025 | 10 | 100 | 100 | 100 | 100 | 100 | 100 | 100 |
| MH-122124 | 10 | 100 | 100 | 100 | 100 | 100 | 100 | 100 |
| MH-122754 | 10 | 100 | 100 | 100 | 100 | 100 | 100 | 100 |
| MH-122755 | 10 | 100 | 100 | 100 | 100 | 100 | 100 | 100 |
| MH-122756 | 10 | 100 | 100 | 100 | 100 | 100 | 100 | 100 |

*)in the case where a microorganism was not contained.
**)in the case where a chemical herbicide was not contained.

TABLE 6-3

Herbicidal Effects by Compositions of New Microorganism Strains According to the Invention and Chemical Herbicides of the Thiolcarbamate Type

| Microorganism | Chemical herbicide ||||
|---|---|---|---|---|
| | —**) | L | M | N | O |
| —*) | 0 | 5 | 10 | 10 | 10 |
| MH-0015 | 0 | 5 | 10 | 10 | 10 |
| MH-9011 | 5 | 10 | 15 | 15 | 15 |
| MH-111010 | 5 | 100 | 100 | 100 | 100 |
| MH-121024 | 5 | 100 | 100 | 100 | 100 |
| MH-121025 | 5 | 100 | 100 | 100 | 100 |
| MH-122124 | 5 | 100 | 100 | 100 | 100 |
| MH-122754 | 5 | 100 | 100 | 100 | 100 |
| MH-122755 | 5 | 100 | 100 | 100 | 100 |
| MH-122756 | 5 | 100 | 100 | 100 | 100 |

*)in the case where a microorganism was not contained.
**)in the case where a chemical herbicide was not contained.

It is appreciated from Table 6-1 that, in the case of the compositions containing the new microorganism strains according to the present invention in combination with the diphenyl ether herbicides, i.e., CNP, chlormethoxynil and bifenox or the diazine herbicide, i.e., oxadiazon, respectively, the herbicidal activities were synergistically enhanced compared with their single application.

It is understood from Table 6-2 that, in the case of the compositions containing the new microorganism strains according to the present invention in combination with the anilide herbicides, i.e., mefenacet, naproanilide, NSK-850, butachlor, pretilachlor, propanil and clomeprop, respectively, the herbicidal activities were synergistically enhanced compared with their single application.

It is envisaged from Table 6-3 that, in the case of the compositions containing the new microorganism strains according to the present invention in combination with the thiolcarbamate herbicides, i.e., benthiocarb, dimepiperate, molinate and esprocarb, respectively, the herbicidal activities were synergistically enhanced compared with their single application.

From the foregoing results, outstanding synergistic effects can be observed from compositions which contain new microorganism strains having pathogenicity against barnyard grass in combination with diphenyl ether herbicides, anilide herbicides, thiolcarbamate herbicides, diazine herbicides or like herbicides, said herbicides having all been employed as barnyard grass herbicides. Consequently, it has become possible to satisfactorily control barnyard grass by using such chemical herbicides even at a dosage as low as one tenth to one hundredth of their conventional dosage.

Example 2

Herbicidal Effects by Weed Control Compositions of New Microorganism Strains According to the Invention and Chemical Herbicides, against Barnyard Grass—Flowable Formulations Barnyard grass seeds were planted in lowland soil which was contained in 1/1000-are pots, and the plants raising from the seeds were reared to the 1.5 leaf stage. The plants were irrigated to keep about 5 cm depth in water and treated with 1 μl (equivalent to one tenth of the standard dosage) of the flowable formulations prepared as described in the above formulation examples 38–41 except that various strains and herbicides were used. The plants were then allowed to grow in a green house which was maintained at 15° C. during the day time and at also at night. Twenty days after the treatment, the remaining populations in the individual pots were counted. The control values against barnyard grass were calculated in accordance with the following formula and are shown in Tables 7-1 to 7-3.

$$\text{Control value} = \frac{\text{Remaining population in untreated group} - \text{Remaining population in treated group}}{\text{Remaining population in untreated group}} \times 100$$

It is appreciated from Table 7-1 that, in the case of the compositions containing the new microorganism strains according to the present invention in combination with the diphenyl ether herbicide, i.e., CNP, respectively, the herbicidal activities were synergistically enhanced compared with their single application.

It is understood from Table 7-2 that, in the case of the compositions containing the new microorganism strains according to the present invention in combination with the anilide herbicides, i.e., mefenacet and pretilachlor, respectively, the herbicidal activities were synergistically enhanced compared with their single application.

It is envisaged from Table 7-3 that, in the case of the compositions containing the new microorganism strains according to the present invention in combination with the thiolcarbamate herbicides, i.e., benthiocarb and molinate, respectively, the herbicidal activities were synergistically enhanced compared with their single application.

TABLE 7-1

Herbicidal Effects by Compositions of New Microorganism Strains According to the Invention and CNP

| Microorganism | Chemical herbicide | |
| --- | --- | --- |
| | —**) | CNP |
| —*) | 0 | 15 |
| MH-0015 | 0 | 10 |
| MH-9011 | 5 | 10 |
| MH-111010 | 10 | 100 |
| MH-121024 | 10 | 100 |
| MH-121025 | 10 | 100 |
| MH-122124 | 10 | 100 |
| MH-122754 | 10 | 100 |
| MH-122755 | 10 | 100 |
| MH-122756 | 10 | 100 |

*)in the case where a microorganism was not contained.
**)in the case where a chemical herbicide was not contained.

TABLE 7-2

Herbicidal Effects by Compositions of New Microorganism Strains According to the Invention, Mefenacet and Pretilachlor

| Microorganism | Chemical herbicide | | |
| --- | --- | --- | --- |
| | —**) | Mefenacet | Pretilachlor |
| —*) | 0 | 15 | 20 |
| MH-0015 | 5 | 15 | 20 |
| MH-9011 | 5 | 20 | 20 |
| MH-111010 | 10 | 100 | 100 |
| MH-121024 | 10 | 100 | 100 |
| MH-121025 | 10 | 100 | 100 |
| MH-122124 | 10 | 100 | 100 |
| MH-122754 | 10 | 100 | 100 |
| MH-122755 | 10 | 100 | 100 |
| MH-122756 | 10 | 100 | 100 |

*)in the case where a microorganism was not contained.
**)in the case where a chemical herbicide was not contained.

TABLE 7-3

Herbicidal Effects by Compositions of New Microorganism Strains According to the Invention, Benthiocarb and Molinate

| Microorganism | Chemical herbicide | | |
| --- | --- | --- | --- |
| | —**) | Benthiocarb | Molinate |
| —*) | 0 | 5 | 10 |
| MH-0015 | 5 | 5 | 10 |
| MH-9011 | 5 | 10 | 10 |
| MH-111010 | 10 | 100 | 100 |
| MH-121024 | 10 | 100 | 100 |
| MH-121025 | 10 | 100 | 100 |
| MH-122124 | 10 | 100 | 100 |
| MH-122754 | 10 | 100 | 100 |
| MH-122755 | 10 | 100 | 100 |
| MH-122756 | 10 | 100 | 100 |

*)in the case where a microorganism was not contained.
**)in the case where a chemical herbicide was not contained.

Example 3

Herbicidal Effects by Weed Control Compositions of New Microorganism Strains According to the Invention and Chemical Herbicides, against Barnyard Grass—Emulsion Barnyard grass seeds were planted in lowland soil which was contained in 1/1000-are pots, and the plants raising from the seeds were reared to the 1.5 leaf stage. The plants were irrigated to keep about 5 cm depth in water and treated with 1.5 µl (equivalent to one tenth of the standard dosage) of the flowable formulations prepared as described in the above formulation examples 45–46 except that various strains and herbicides were used. The plants were then allowed to grow in a green house which was maintained at 15° C. during the day time and also at night. Twenty days after the treatment, the remaining populations in the individual pots were counted. The control values against barnyard grass were calculated in accordance with the following formula and are shown in Table 8.

$$\text{Control value} = \frac{\text{Remaining population in untreated group} - \text{Remaining population in treated group}}{\text{Remaining population in untreated group}} \times 100$$

In the table, A, E, I and L represent the following herbicides at the dosages in the parentheses.

| | Dosage (g/10 are) |
| --- | --- |
| A: CNP | (27) |
| E: Mefenacet | (12) |
| I: Pretilachlor | (6) |
| L: Benthiocarb | (21) |

It is appreciated from Table 8 that, in the case of the compositions containing the new microorganism strains according to the present invention in combination with the diphenyl ether herbicide, i.e., CNP, respectively, the herbicidal activities were synergistically enhanced compared with their single application.

It is understood from Table 8 that, in the case of the compositions containing the new microorganism strains according to the present invention in combination with the anilide herbicides, i.e., mefenacet and pretilachlor, respectively, the herbicidal activities were synergistically enhanced compared with their single application.

It is envisaged from Table 8 that, in the case of the compositions containing the new microorganism strains according to the present invention in combination with the thiolcarbamate herbicides, i.e., benthiocarb and molinate, respectively, the herbicidal activities were synergistically enhanced compared with their single application.

TABLE 8

Herbicidal Effects by Compositions of New Microorganism Strains According to the Invention and Chemical Herbicides

| Microorganism | Chemical herbicide | | | | |
| --- | --- | --- | --- | --- | --- |
| | —**) | A | E | I | L |
| —*) | 0 | 5 | 10 | 10 | 10 |
| MH-0015 | 0 | 5 | 10 | 10 | 10 |

TABLE 8-continued

Herbicidal Effects by Compositions of New Microorganism Strains According to the Invention and Chemical Herbicides

| Microorganism | —**) | A | E | I | L |
|---|---|---|---|---|---|
| | | | Chemical herbicide | | |
| MH-9011 | 10 | 10 | 15 | 20 | 15 |
| MH-111010 | 10 | 100 | 100 | 100 | 100 |
| MH-121024 | 10 | 100 | 100 | 100 | 100 |
| MH-121025 | 10 | 100 | 100 | 100 | 100 |
| MH-122124 | 10 | 100 | 100 | 100 | 100 |
| MH-122754 | 10 | 100 | 100 | 100 | 100 |
| MH-122755 | 10 | 100 | 100 | 100 | 100 |
| MH-122756 | 10 | 100 | 100 | 100 | 100 |

*)in the case where a microorganism was not contained.
**)in the case where a chemical herbicide was not contained.

Example 4

Herbicidal Effects by Weed Control Compositions of New Microorganism Strains According to the Invention and Chemical Herbicides, against Barnyard Grass and Broadleaf Weeds Barnyard grass, monochoria (*Monochoria vaginalis*) and narrowleaf waterplantain were separately seeded in lowland soil which was contained in 1/1000-are pots and were reared to the 1.5 leaf stage. The pots which were in a state irrigated to about 3 cm in water depth were treated with 1.5 mg (equivalent to one tenth of the standard dosage) of the various compositions prepared as described in Formulation Examples 24–31 except that various strains and herbicides were used. The seedlings were then allowed to grow in a green house which was maintained at 15° C. during the day time and also at night. Twenty days after the treatment, the remaining populations in the individual pots were counted. The control values against barnyard grass, monochoria or narrowleaf waterplantain were calculated in accordance with the following formula and are shown in Tables 9-1 to 9-3.

$$\text{Control value} = \frac{\text{Remaining population in untreated group} - \text{Remaining population in treated group}}{\text{Remaining population in untreated group}} \times 100$$

In the tables, P-S represent the following herbicides at the following dosages in the parentheses.

| | Dosage (g/10 are) |
|---|---|
| P: Bensulfuron methyl | (0.7) |
| Q: Pyrazosulfron ethyl | (0.2) |
| R: Pyrazolate | (30) |
| S: Simetryne | (7.5) |

TABLE 9-1

Herbicidal Effects by Compositions of New Microorganism Strains According to the Invention and Chemical Herbicides against Barnyard Grass

| Microorganism | —**) | P | Q | R | S |
|---|---|---|---|---|---|
| | | | Chemical herbicide | | |
| —*) | 0 | 10 | 10 | 15 | 5 |
| MH-0015 | 0 | 10 | 10 | 15 | 10 |
| MH-9011 | 5 | 15 | 15 | 20 | 10 |
| MH-111010 | 10 | 100 | 100 | 100 | 100 |
| MH-121024 | 10 | 100 | 100 | 100 | 100 |
| MH-121025 | 10 | 100 | 100 | 100 | 100 |
| MH-122124 | 10 | 100 | 100 | 100 | 100 |
| MH-122754 | 10 | 100 | 100 | 100 | 100 |
| MH-122755 | 10 | 100 | 100 | 100 | 100 |
| MH-122756 | 10 | 100 | 100 | 100 | 100 |

*)in the case where a microorganism was not contained.
**)in the case where a chemical herbicide was not contained.

TABLE 9-2

Herbicidal Effects by Compositions of New Microorganism Strains According to the Invention and Chemical Herbicides against Monochoria

| Microorganism | —**) | P | Q | R | S |
|---|---|---|---|---|---|
| | | | Chemical herbicide | | |
| —*) | 0 | 85 | 85 | 80 | 90 |
| MH-0015 | 0 | 90 | 90 | 90 | 90 |
| MH-9011 | 0 | 85 | 85 | 85 | 85 |
| MH-111010 | 5 | 100 | 100 | 100 | 100 |
| MH-121024 | 5 | 100 | 100 | 100 | 100 |
| MH-121025 | 5 | 100 | 100 | 100 | 100 |
| MH-122124 | 5 | 100 | 100 | 100 | 100 |
| MH-122754 | 5 | 100 | 100 | 100 | 100 |
| MH-122755 | 5 | 100 | 100 | 100 | 100 |
| MH-122756 | 5 | 100 | 100 | 100 | 100 |

*)in the case where a microorganism was not contained.
**)in the case where a chemical herbicide was not contained.

TABLE 9-3

Herbicidal Effects by Compositions of New Microorganism Strains and Chemical Herbicides Against Narrowleaf Waterplantain

| Microorganism | —**) | P | Q | R | S |
|---|---|---|---|---|---|
| | | | Chemical herbicide | | |
| —*) | 0 | 85 | 85 | 80 | 90 |
| MH-0015 | 0 | 90 | 90 | 90 | 90 |
| MH-9011 | 0 | 85 | 85 | 85 | 85 |
| MH-111010 | 5 | 100 | 100 | 100 | 100 |
| MH-121024 | 5 | 100 | 100 | 100 | 100 |
| MH-121025 | 5 | 100 | 100 | 100 | 100 |
| MH-122124 | 5 | 100 | 100 | 100 | 100 |
| MH-122754 | 5 | 100 | 100 | 100 | 100 |
| MH-122755 | 5 | 100 | 100 | 100 | 100 |
| MH-122756 | 5 | 100 | 100 | 100 | 100 |

*)in the case where a microorganism was not contained.
**)in the case where a chemical herbicide was not contained.

It is appreciated from Table 9-1 that, in the case of the compositions containing the new microorganism strains according to the present invention in combination with the sulfonyl urea herbicides, i.e., bensulfuron methyl and pyrazosulfron ethyl, the diazine herbicide, i.e., pyrazolate or the triazine herbicide, i.e., simetryne, respectively, the herbicidal activities against barnyard grass were synergistically enhanced compared with their single application.

It is understood from Tables 9-2 and 9-3 that, in the case of the compositions containing the new microorganism strains according to the present invention in combination with the sulfonyl urea herbicides, i.e., bensulfuron methyl and pyrazosulfron ethyl, the diazine herbicide, i.e., pyrazolate or the triazine herbicide, i.e., simetryne, respectively, the herbicidal activities against the broadleaf weeds, namely, monochoria or narrowleaf waterplantain were enhanced to some extent compared with their single application.

It is also envisaged that, in the case of the compositions containing the new microorganism strains according to the present invention in combination with the sulfonyl urea herbicides, i.e., bensulfuron methyl and pyrazosulfron ethyl, the diazine herbicide, i.e., pyrazolate or the triazine herbicide, i.e., simetryne, respectively, sufficient weed control effects were also exhibited against the broadleaf weeds, namely, monochoria or narrowleaf waterplantain compared with their single application and increased practical utility was observed.

From the foregoing results, it is understood that compositions containing new microorganism strains of the present invention having pathogenicity against barnyard grass in combination with sulfonyl urea herbicides such as bensulfuron methyl and pyrazosulfron ethyl, diazine herbicides such as pyrazolate or triazine herbicides such as simetryne—said herbicides having been employed against broadleaf weeds—can exhibit enhanced weed control effects against barnyard grass and also a broadened spectrum and enhanced herbicidal effects against broadleaf weeds although the enhancement of their herbicidal effects against broadleaf weeds is not substantial. These compositions are therefore believed to have practical utility.

The combined use with broadleaf weed herbicides makes it possible to reduce the dosage of conidia of new microorganism of the present invention. This in turn makes it possible to reduce the production cost.

Example 5

Dosage Reduction of Conidia by Synergistic Effects of New Microorganism Strains According to the Invention and Chemical Herbicides Barnyard grass seeds were planted in lowland soil which was contained in 1/1000-are pots, and the plants raising from the seeds were reared to the 1.5 leaf stage. The plants were irrigated to keep about 5 cm depth in water and treated with predetermined amounts of conidia and also with a prescribed amount (equivalent to one tenth of the standard dosage) of the broadleaf weed herbicide, bensulfuron. The plants were then allowed to grow in a green house which was maintained at 15° C. during the day time and also at night. Twenty days after the treatment, the remaining populations in the individual pots were counted. The control values against barnyard grass were calculated in accordance with the following formula and are shown in Table 10.

$$\text{Control value} = \frac{\text{Remaining population in untreated group} - \text{Remaining population in treated group}}{\text{Remaining population in untreated group}} \times 100$$

TABLE 10

Reduction in Conidium Dosage owing to Synergistic Effects of New Microorganism Strains According to the Invention and Chemical Herbicides

| Microorganism MH-111010 | Microorganism alone | Bensulfuron + Microorganism |
|---|---|---|
| $3 \times 10^5$ | 100 | 100 |
| $1 \times 10^5$ | 95 | 100 |
| $3 \times 10^4$ | 55 | 100 |
| $1 \times 10^4$ | 30 | 100 |
| $3 \times 10^3$ | 5 | 70 |
| 0 | 0 (Untreated) | 10 (Herbicide alone) |

What is claimed is:

1. A weed control composition comprising at least one strain of *Drechslera monoceras* var. *microsporus*, an effective amount of at least one chemical herbicide and an agriculturally-acceptable carrier or diluent, said strain being free of pathogenicity against crops but having pathogenicity against barnyard grass and having the zymogrammatic pattern of esterases shown in FIG. 1 and being contained in an amount sufficient to provide weed control effects.

2. A weed control composition of claim 1, wherein the strain of *Drechslera monoceras* var. *microsporus* is FERM BP-3864, FERM BP-4498, FERM BP-4499, FERM BP-4500, FERM BP-4501, FERM BP-4502 or FERM BP-4503.

3. A weed control composition of claim 1, wherein the chemical herbicide is at least one chemical herbicide selected from the group consisting of diphenyl ether herbicides, anilide herbicides, thiolcarbamate herbicides, diazine herbicides, sulfonylurea herbicides and triazine herbicides.

4. A weed control composition of claim 1, wherein the chemical herbicide is at least one diphenyl ether herbicide selected from the group consisting of CNP (chemical name: 2,4,6-trichlorophenyl-4-nitrophenyl ether), chlormethoxynil (chemical name: 2,4-dichlorophenyl-4-nitro-3-methoxyphenyl ether) and bifenox (chemical name: 2,4-dichlorophenyl-3-methoxycarbonyl-4-phenylether).

5. A weed control composition of claim 1, wherein the chemical herbicide is at least one anilide herbicide selected from the group consisting of mefenacet (chemical name: 2-benzothiazol-3-yloxy-N-methylacetanilide), pretilachlor (chemical name: 2-chloro-2',6'-diethyl-N-(n-propoxyethyl)acetanilide), naproanilide (chemical name: 2-(2-naphthoxy)propionic anilide), NSK-850 (chemical name: N-[2,7-(3'-methoxy) -thienylmethyl-N-chloroaceto-2,6-dimethylanilide), butachlor (chemical name: 2-chloro-2',6'-diethyl-N(butoxymethyl)acetanilide), propanil (chemical name: 3',4'-dichloropropionanilide) and clomeprop (chemical name: 2-(2,4-dichloro-3-methylphenoxy)propionanilide).

6. A weed control composition of claim 1, wherein the chemical herbicide is at least one thiolcarbamate herbicide selected from the group consisting of benthiocarb (chemical name: S-(4-chlorobenzyl)-N,N-diethylthiolcarbamate), dimepiperate (chemical name: S-(1-methyl-1-phenethyl)-piperidine-1-carbathioate), molinate (chemical name: S-ethyl-N,N-hexamethylenethiolcarbamate) and esprocarb (chemical name: S-benzyl-N-ethyl-N-(1,2-dimethylpropyl)thiolcarbamate).

7. A weed control composition of claim 1, wherein the chemical herbicide is oxadiazon (chemical name: 5-tert-butyl-3-(2,4-dichloro-5-isopropoxyphenyl)-1,3,4-oxazol- 2(3H)-one) or pyrazolate (chemical name: 4-(2,4-dichlorobenzoyl)-1,3-dimethyl-1H-pyrazol-5-yl-p-toluenesulfonate), or a mixture thereof.

8. A weed control composition of claim 1, wherein the chemical herbicide is bensulfuron methyl (chemical name: methyl 2-[3-(4,6-dimethyl-pyrimidin-2-yl)ureidosulfonylmethyl] benzoate) or pyrazosulfuron ethyl (chemical name: ethyl 5-[3-(4,6-dimethoxy -pyrimidin-2-yl)ureidosulfonyl]-1-methylpyrazole-4-carboxylate), or a mixture thereof.

9. A weed control composition of claim 1, wherein the chemical herbicide is simetryne (chemical name: 2,4-bis-(ethylamino)-6-methylthio-1,3,5-triazine).

10. A weed control method, which comprises, for the purpose of controlling barnyard grass, applying an effective amount of at least one strain of *Drechslera monoceras* var. *microsporus* and at least one chemical herbicide to a place where the control is needed, said strain being free of pathogenicity against crops but having pathogenicity against barnyard grass and having the zymogramatic pattern of esterases shown in FIG. 1.

11. A weed control method of claim 10, wherein the strain of *Drechslera monoceras* var. *microsporus* is FERM BP-3864, FERM BP-4498, FERM BP-4499, FERM BP-4500, FERM BP-4501, FERM BP-4502 or FERM BP-4503.

12. A weed control method of claim 10, wherein the chemical herbicide is at least one chemical herbicide selected from the group consisting of diphenyl ether herbicides, anilide herbicides, thiolcarbamate herbicides, diazine herbicides, sulfonylurea herbicides and triazine herbicides.

13. A weed control method of claim 10, wherein the chemical herbicide is at least one diphenyl ether herbicide selected from the group consisting of CNP (chemical name: 2,4,6-trichlorophenyl-4-nitrophenyl ether), chlormethoxynil (chemical name: 2,4-dichlorophenyl-4-nitro-3-methoxyphenyl ether) and bifenox (chemical name: 2,4-dichlorophenyl-3-methoxycarbonyl-4-phenylether).

14. A weed control method of claim 10, wherein the chemical herbicide is at least one anilide herbicide selected from the group consisting of mefenacet (chemical name: 2-benzothiazol-2-yloxy-N-methylacetanilide), pretilachlor (chemical name: 2-chloro 2',6'-diethyl-N-(n-propoxyethyl)acetanilide), naproanilide (chemical name: 2-(2-naphthoxy)propionic anilide), NSK-850 (chemical name: N-[2,7-(3'-methoxy) -thienylmethyl-N-chloroaceto-2,6-dimethylanilide), butachlor (chemical name: 2-chloro-2',6'-diethyl-N (butoxymethyl)acetanilide), propanil (chemical name: 3',4'-dichloropropionanilide) and clomeprop (chemical name: 2-(2,4-dichloro-3-methylphenoxy)propionanilide).

15. A weed control method of claim 10, wherein the chemical herbicide is at least one thiolcarbamate herbicide selected from the group consisting of benthiocarb (chemical name: S-(4-chlorobenzyl)-N,N-diethylthiolcarbamate), dimepiperate (chemical name: S -(1-methyl-1-phenethyl)-piperidine-1-carbathioate), molinate (chemical name: S-ethyl-N,N-hexamethylenethiolcarbamate) and esprocarb (chemical name: S-benzyl -N-ethyl-N-(1,2-dimethylpropyl)thiolcarbamate).

16. A weed control method of claim 10, wherein the chemical herbicide is oxadiazon (chemical name: 5 -tert-butyl-3-(2,4-dichloro-5-isopropoxyphenyl)-1,3,4 -oxazol-2(3H)-one) or pyrazolate (chemical name: 4-(2,4 -dichlorobenzoyl)-1,3-dimethyl-1H-pyrazol-5-yl-p-toluenesulfonate), or a mixture thereof.

17. A weed control method of claim 10, wherein the chemical herbicide is bensulfuron methyl (chemical name: methyl-2-[3-(4,6-dimethyl-pyrimidin-2-yl)ureidosulfonyl-methyl] benzoate) or pyrazosulfuron ethyl (chemical name: ethyl 5-[3-(4,6-dimethoxypyrimidin -2-yl)ureidosulfonyl]-1-methylpyrazole-4-carboxylate), or a mixture thereof.

18. A weed control method of claim 10, wherein the chemical herbicide is simetryne (chemical name: 2,4-bis-(ethylamino)-6-methylthio-1,3,5-triazine).

* * * * *